United States Patent
Marinković et al.

(10) Patent No.: US 8,410,288 B2
(45) Date of Patent: Apr. 2, 2013

(54) POLYMORPHS OF SAXAGLIPTIN HYDROCHLORIDE AND PROCESSES FOR PREPARING THEM

(75) Inventors: Marina Marinković, Sesvete-Zagreb (HR); Marina Ratkaj, Zagreb (HR); Oliver Franković, Vodice (HR); Tina Mundorfer, Zagreb (HR)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 13/252,682

(22) Filed: Oct. 4, 2011

(65) Prior Publication Data

US 2012/0083517 A1 Apr. 5, 2012

Related U.S. Application Data

(60) Provisional application No. 61/389,399, filed on Oct. 4, 2010, provisional application No. 61/415,017, filed on Nov. 18, 2010, provisional application No. 61/418,951, filed on Dec. 2, 2010, provisional application No. 61/424,889, filed on Dec. 20, 2010, provisional application No. 61/436,747, filed on Jan. 27, 2011, provisional application No. 61/448,316, filed on Mar. 2, 2011, provisional application No. 61/467,125, filed on Mar. 24, 2011, provisional application No. 61/482,362, filed on May 4, 2011, provisional application No. 61/484,761, filed on May 11, 2011.

(51) Int. Cl.
  *C07D 209/02* (2006.01)
  *A61K 31/403* (2006.01)
(52) U.S. Cl. .................................. 548/452; 514/412
(58) Field of Classification Search ................ None
  See application file for complete search history.

(56) References Cited

U.S. PATENT DOCUMENTS

| | | |
|---|---|---|
| 6,395,767 B2 | 5/2002 | Robl et al. |
| 6,995,183 B2 | 2/2006 | Hamann et al. |
| 7,186,846 B2 | 3/2007 | Sharma et al. |
| 7,214,702 B2 | 5/2007 | Sharma |
| 7,223,573 B2 | 5/2007 | Patel et al. |
| 7,420,079 B2 | 9/2008 | Vu et al. |
| 7,470,810 B2 | 12/2008 | Sharma et al. |
| 7,741,082 B2 | 6/2010 | Politino et al. |
| 7,943,656 B2 | 5/2011 | Gougoutas et al. |
| 2006/0035954 A1 | 2/2006 | Sharma et al. |

FOREIGN PATENT DOCUMENTS

| | | |
|---|---|---|
| WO | WO-01/68603 | 9/2001 |
| WO | WO-2008/131149 | 10/2008 |
| WO | WO-2010/115974 | 10/2010 |
| WO | WO-2011/140328 | 11/2011 |

OTHER PUBLICATIONS

Savage, Scott A., et al., "Preparation of Saxagliptin, a Novel DPP-IV Inhibitor", Organic Process Research & Development, 2009, vol. 13, pp. 1169-1176.
Advanced Synthesis & Catalysis (2007), 349 (8+9), 1369-1378; Author(s): Ronald L. Hanson, et al., Bristol-Meyers Squibb Company.
Journal of Medicinal Chemistry (2005), 48, 5025-5037, Authors: David J. Augeri et al., Bristol-Meyers Squibb Company.
Drugs of the Future (2008), 33(7), 577-586, Authors: P. Cole, J. Bolós, R. Castañer, Bristol-Meyers Squibb Company.
Enzyme and Microbial Technology (2011), 48, 445-453, Authors: R. L. Hanson, R. M. Johnston, S.L. Goldberg, W. L. Parker, R. N. Patel, Bristol-Meyers Squibb Company.
IPCOM000195128D, Electronic Publication Apr. 21, 2010, 3 pages.
IPCOM000197291D, Electronic Publication Jul. 1, 2010, 3 pages.
Caira, Mino R., "Crystalline Polymorphism of Organic Compounds", Topics in Current Chemistry, 1998, vol. 198, pp. 163-208.

*Primary Examiner* — Kamal Saeed
*Assistant Examiner* — Nyeemah A Grazier
(74) *Attorney, Agent, or Firm* — Kenyon & Kenyon LLP

(57) ABSTRACT

The invention provides polymorphs of Saxagliptin hydrochloride, processes for preparing polymorphs of Saxagliptin hydrochloride, and pharmaceutical compositions of polymorphs of Saxagliptin hydrochloride.

19 Claims, 24 Drawing Sheets

POLYMORPHS OF SAXAGLIPTIN HYDROCHLORIDE AND PROCESSES FOR PREPARING THEM

RELATED APPLICATIONS

This application claims the benefit under 35 U.S.C. §119(e) of U.S. Provisional Application Nos. 61/389,399, filed on Oct. 4, 2010; 61/415,017, filed on Nov. 18, 2010; 61/418,951, filed on Dec. 2, 2010; 61/424,889, filed on Dec. 20, 2010; 61/436,747, filed on Jan. 27, 2011; 61/448,316, filed on Mar. 2, 2011; 61/467,125, filed on Mar. 24, 2011; 61/482,362, filed on May 4, 2011; and 61/484,761, filed on May 11, 2011.

FIELD OF THE INVENTION

The invention relates to polymorphs of Saxagliptin hydrochloride, processes for preparing them, and pharmaceutical compositions thereof.

BACKGROUND OF THE INVENTION

Saxagliptin, (1S,3S,5S)-2-(2S)-2-Amino-2-(3-hydroxyadamantan-1-yl)-acetyl)-2-azabicyclo[3.1.0]hexane-3-carbonitrile of the following chemical structure:

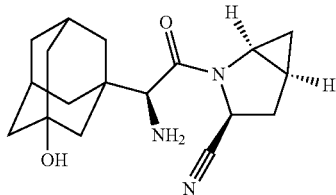 [SMILES: N#C[C@@H]1C[C@@H]2C[C@@H]2N1C(=O)[C@@H](N)C12CC3CC(CC(O)(C3)C1)C2]

is a dipeptidyl peptidase IV (DPP4) inhibitor. Saxagliptin is marketed under the trade name ONGLYZA® by Bristol-Myers Squibb for the treatment of type 2 diabetes.

Saxagliptin and its hydrochloride and trifluoroacetic acid salts are disclosed in U.S. Pat. No. 6,395,767. In addition, U.S. Pat. No. 7,420,079 discloses Saxagliptin and its hydrochloride, trifluoroacetic acid and benzoate salts, as well as Saxagliptin monohydrate.

U.S. 2009/054303 and the corresponding WO 2008/131149 application disclose several crystalline forms of Saxagliptin and of Saxagliptin salts. The crystalline forms of Saxagliptin reported in that patent application are a monohydrate (denoted there as form H-1), a hemihydrate (denoted there as form H0.5-2), a dihydrate (denoted form H2-1) and an anhydrous form (denoted there as N-3).

WO 2005/117841 (the '841 application) describes the cyclization of Saxagliptin to form the therapeutically inactive cyclic amidine. The '841 application reports that such cyclization can occur both in solid state and solution state.

WO 2010/115974 discloses Forms: I-S, HT-S, IV-S, and HT-IV-S of Saxagliptin hydrochloride.

Polymorphism, the occurrence of different crystal forms, is a property of some molecules and molecular complexes. A single molecule, like Saxagliptin, may give rise to a variety of polymorphic forms having distinct crystal structures and physical properties like melting point, X-ray diffraction pattern, infrared absorption fingerprint, and solid state NMR spectrum. One polymorphic form may give rise to thermal behavior different from that of another polymorphic form. Thermal behavior can be measured in the laboratory by such techniques as capillary melting point, thermogravimetric analysis (TGA), and differential scanning calorimetry (DSC) as well as content of solvent in the polymorphic form, which have been used to distinguish polymorphic forms.

The difference in the physical properties of different polymorphic forms results from the orientation and intermolecular interactions of adjacent molecules or complexes in the bulk solid. Accordingly, polymorphs are distinct solids sharing the same molecular formula yet having distinct advantageous physical properties compared to other polymorphic forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment.

The discovery of new polymorphic forms of Saxagliptin provides new opportunities to improve the synthesis and the characteristics of the active pharmaceutical ingredient (API). It enlarges the repertoire of materials that a formulation scientist has available for designing, for example, a pharmaceutical dosage form of a drug with a targeted release profile or other desired characteristic.

Therefore, there is a need for additional solid state forms of Saxagliptin, and additional methods for preparing Saxagliptin crystal forms that provide Saxagliptin efficiently and can be applied in an industrial scale.

SUMMARY OF THE INVENTION

The invention encompasses novel solid state forms of Saxagliptin hydrochloride, referred to herein as Forms K, T, Z, N, S, O, B, C and D; an amorphous Saxagliptin hydrochloride; processes for preparing the novel solid state forms of Saxagliptin hydrochloride; and formulations comprising the novel solid state forms of Saxagliptin hydrochloride.

The invention further encompasses the above described solid state forms of Saxagliptin hydrochloride for use in the manufacture of a medicament for the treatment of type 2 diabetes.

DETAILED DESCRIPTION OF THE INVENTION

Figure 1:
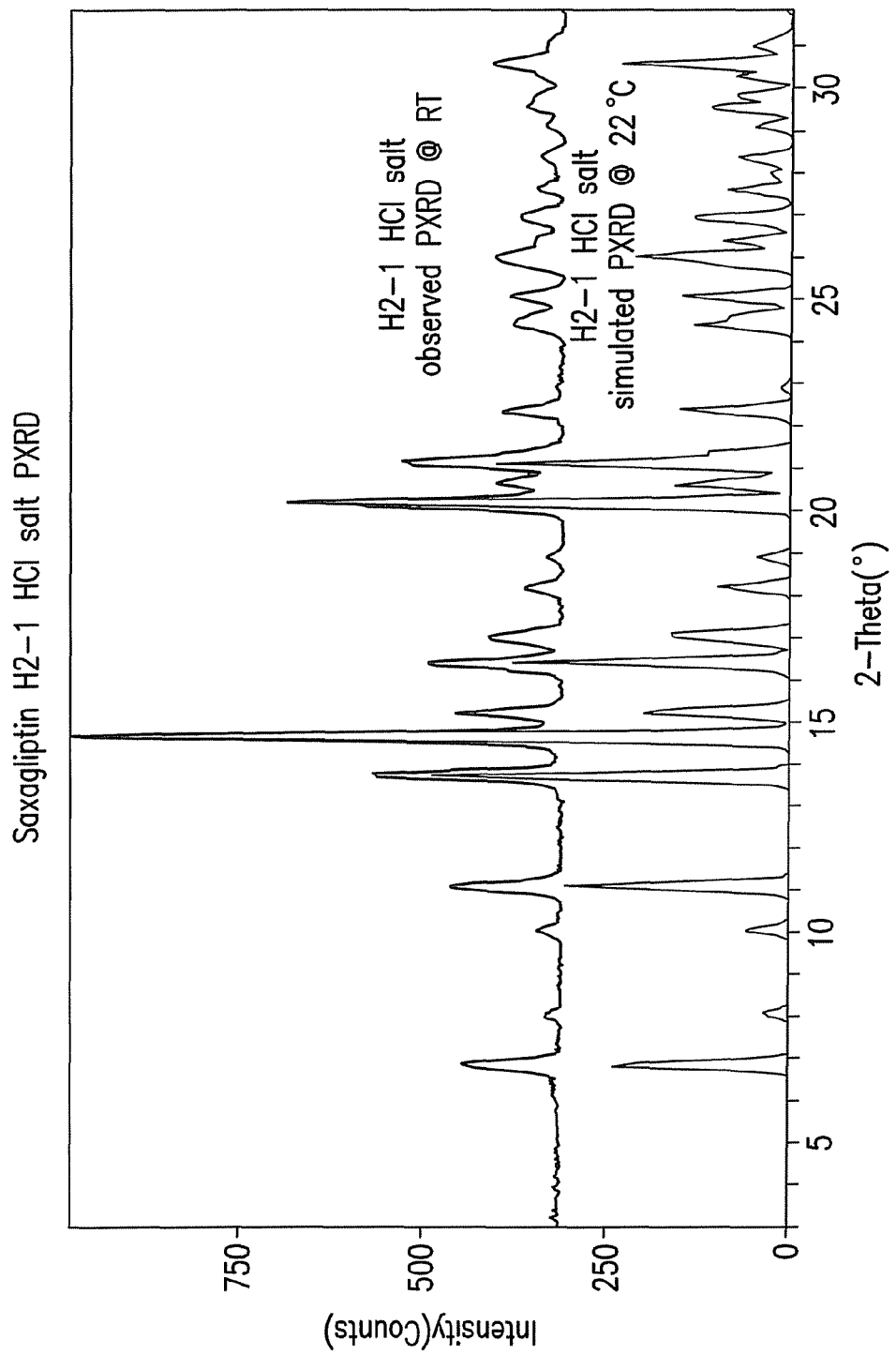
FIG. 1 shows a powder X-ray diffraction (XRD) pattern of crystalline Saxagliptin monohydrochloride dihydrate H2-1. (As reported in US 2009/054303)

The invention relates to polymorphs of Saxagliptin hydrochloride, processes for preparing them, and pharmaceutical compositions thereof.

The solid state forms of the present invention has advantageous properties selected from at least one of: chemical purity, flowability, solubility, morphology or crystal habit, stability—such as storage stability, stability to dehydration, stability to polymorphic conversion, low hygroscopicity, low content of residual solvents.

A crystal form may be referred to herein as being characterized by graphical data "as depicted in" a Figure. Such data include, for example, powder X-ray diffiactograms, FTIR spectra, and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form (or polymorph) may be referred to herein as substantially free of any other crystalline (or polymorphic) forms. As used herein in this context, the expression "substantially free" will be understood to mean that the crystalline form contains 20% or less, 10% or less, 5% or less, 2% or less, or 1% or less of any other form of the subject compound as measured, for example, by XRPD. Thus, polymorphs of Saxagliptin or Saxagliptin hydrochloride described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Saxagliptin or Saxagliptin hydrochloride. Accordingly, in some embodiments of the invention, the described polymorphs of Saxagliptin or Saxagliptin hydrochloride may contain from 1% to 20% (w/w), from 5% to 20% (w/w), or from 5% to 10% (w/w) of one or more other crystal forms of Saxagliptin or Saxagliptin hydrochloride.

In certain embodiments, the described polymorphic form of Saxagliptin or Saxagliptin hydrochloride may be in a composition which comprises the subject polymorphic form of crystalline Saxagliptin or Saxagliptin hydrochloride and one or more other crystal forms of Saxagliptin or Saxagliptin hydrochloride in the above described amounts. In particular, the described polymorphic form of Saxagliptin or Saxagliptin hydrochloride may be in a composition which contains essentially the subject polymorphic form of crystalline Saxagliptin or Saxagliptin hydrochloride and one or more other crystal forms of Saxagliptin or Saxagliptin hydrochloride in the above described amounts.

As used herein, PXRD measurements were obtained using Cu radiation having wavelength 1.54184 Å.

Figure 2:
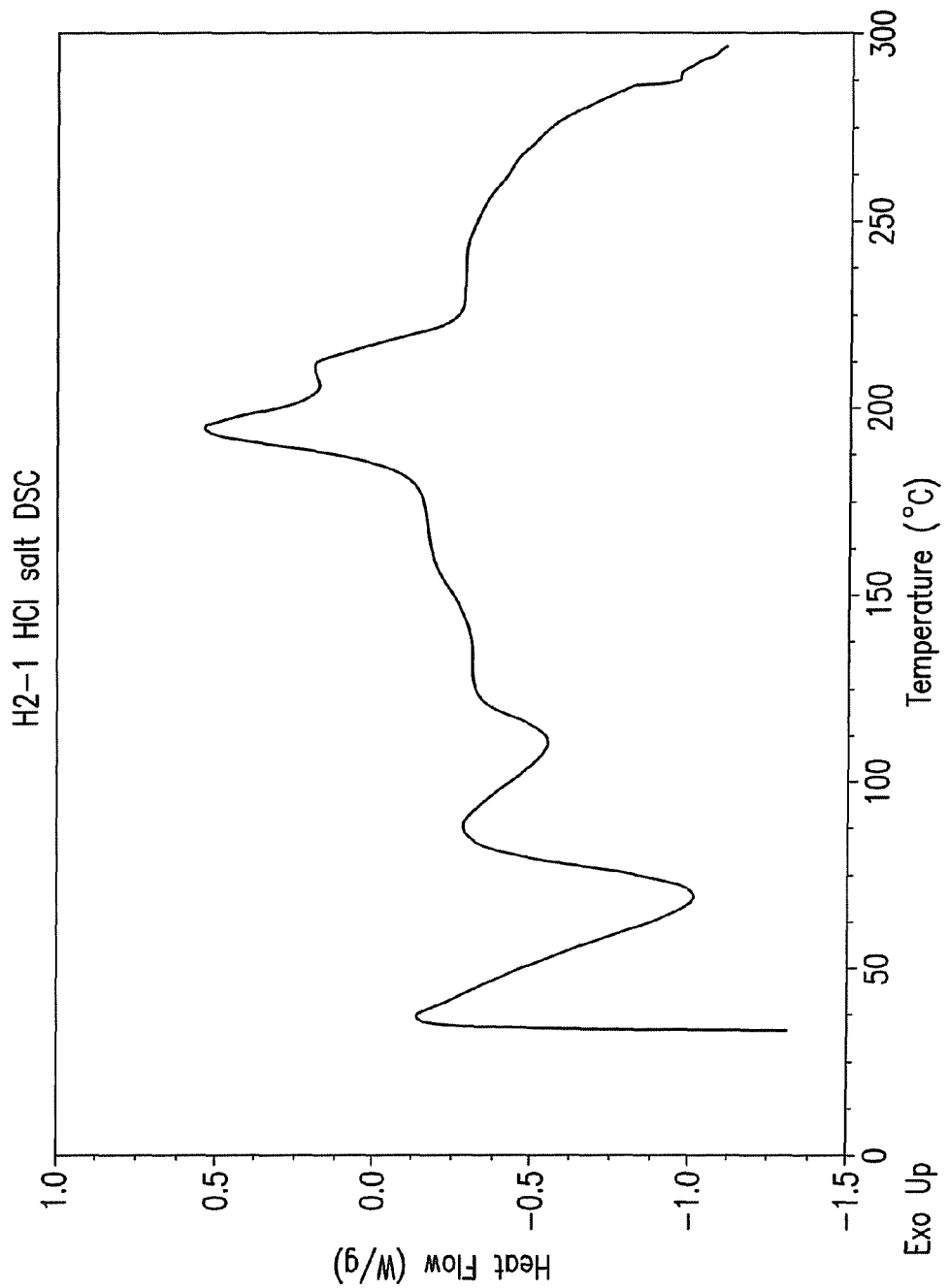
FIG. 2 shows a DSC thermogram of crystalline Saxagliptin monohydrochloride dihydrate H2-1. (As reported in US 2009/054303)

As used herein, the term crystalline Saxagliptin hydrochloride dihydrate form H2-1 refers to a crystalline Saxagliptin hydrochloride dihydrate form H2-1 as characterized by suitable analytical data. Suitable analytical data may include, for example: a powder XRD pattern having peaks at 6.8, 11.1, 13.7, 14.6, 15.2, 16.4, 17.0, 20.2 and 21.1 degrees 2-theta±0.1 degrees 2-theta; a powder X-ray diffraction (PXRD) pattern substantially as depicted in FIG. 1, a DSC pattern substantially as depicted in FIG. 2; a selection of characteristic peaks from the FIG. 1 PXRD pattern or the FIG. 2 DSC pattern that distinguish form H2-1 from other forms of crystalline Saxagliptin hydrochloride dihydrate; or combinations of these analytical data.

Figure 13:
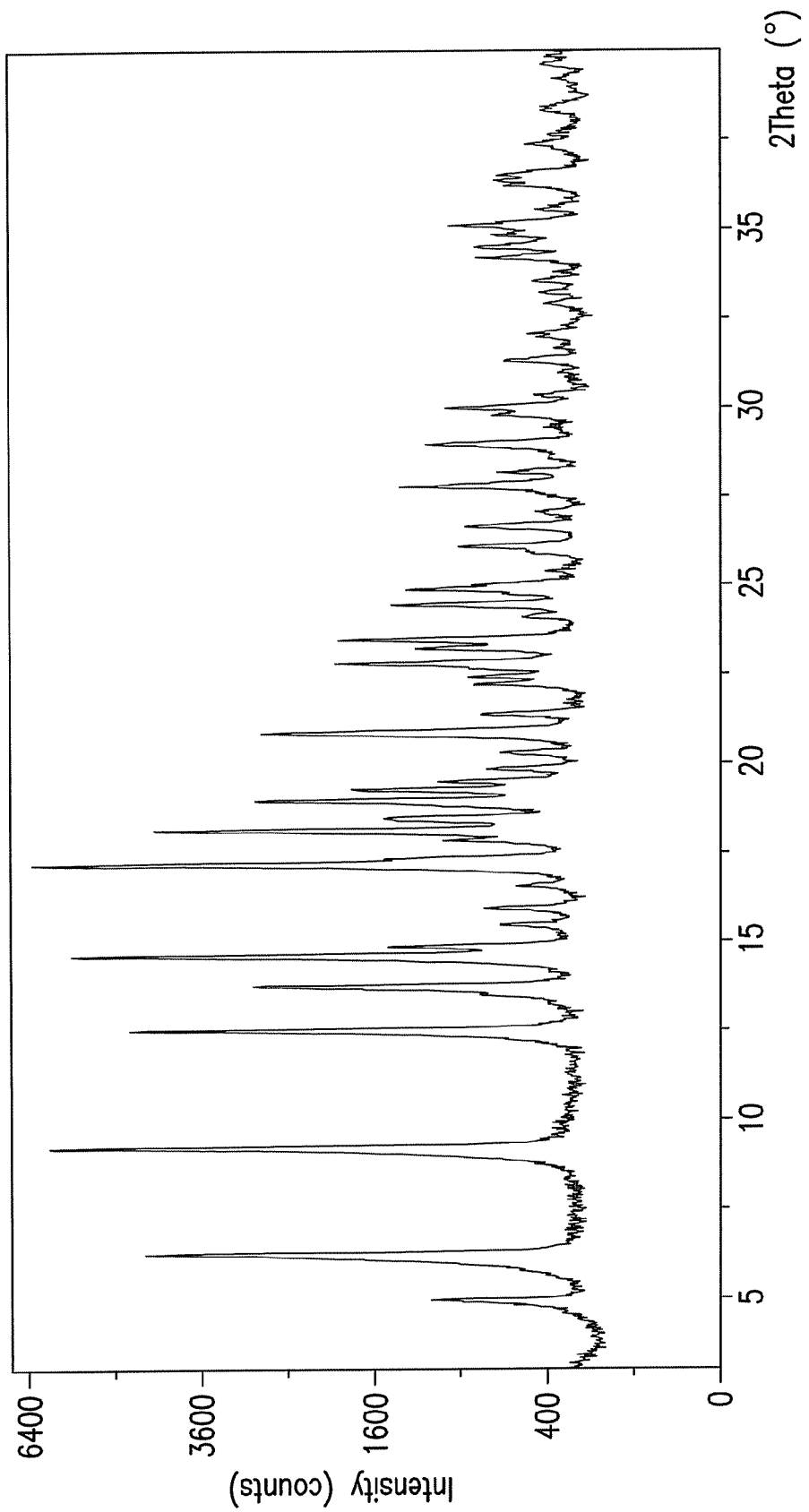
FIG. 13 shows a powder XRD pattern of crystalline Saxagliptin hydrochloride form H1.25-2.

As used herein, the term crystalline Saxagliptin hydrochloride form 111.25-2 refers to a crystalline Saxagliptin hydrochloride characterized by suitable analytical data. Suitable analytical data may include, for example: a powder X-ray diffraction (PXRD) pattern substantially as depicted in FIG. 13; a selection of characteristic peaks from the FIG. 13 PXRD pattern that distinguish form H1.25-2 from other forms of crystalline Saxagliptin hydrochloride; or combinations of these analytical data.

Figure 14:
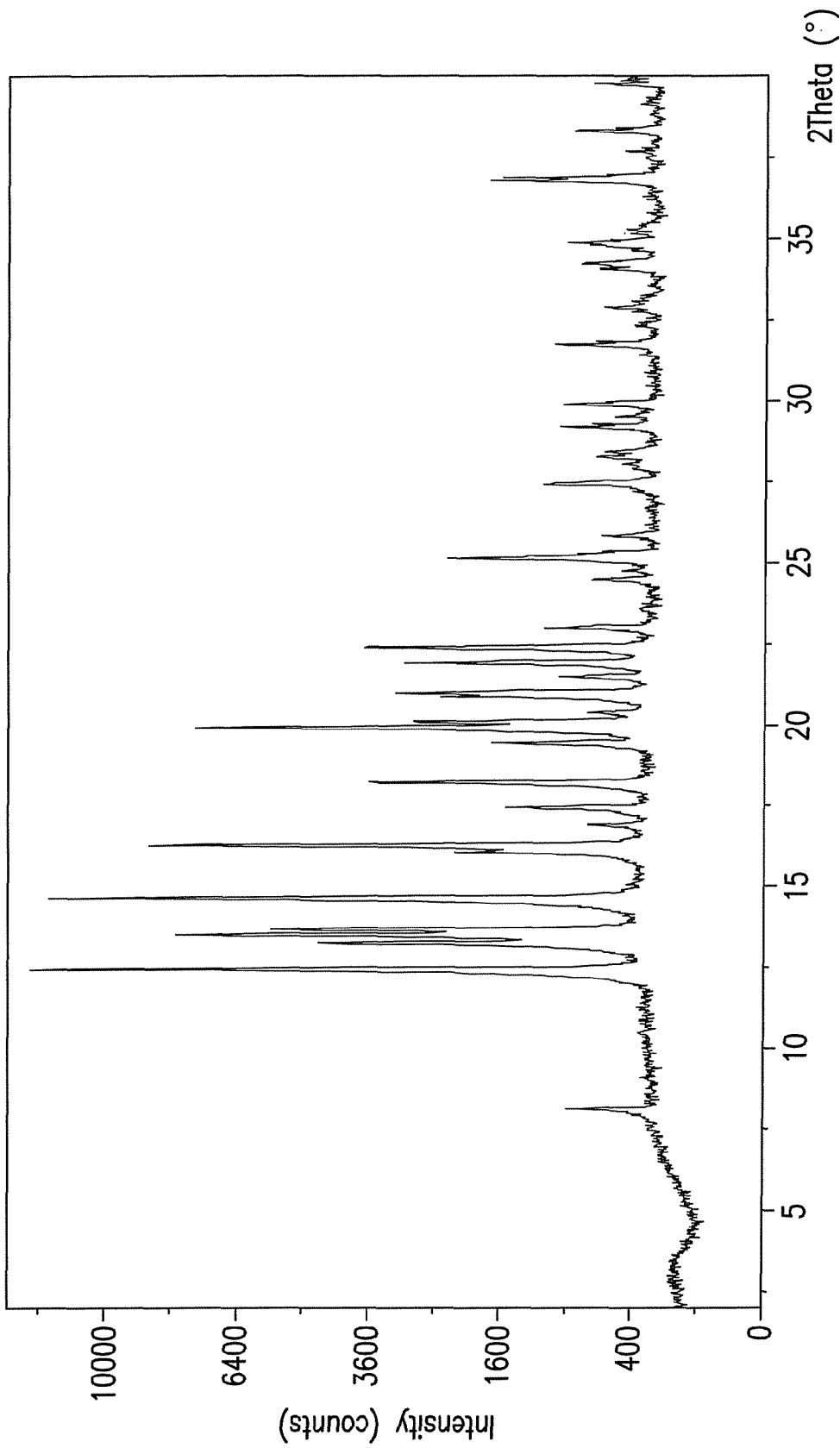
FIG. 14 shows a powder XRD pattern of crystalline Saxagliptin monohydrate fowl H-1.
Figure 15:
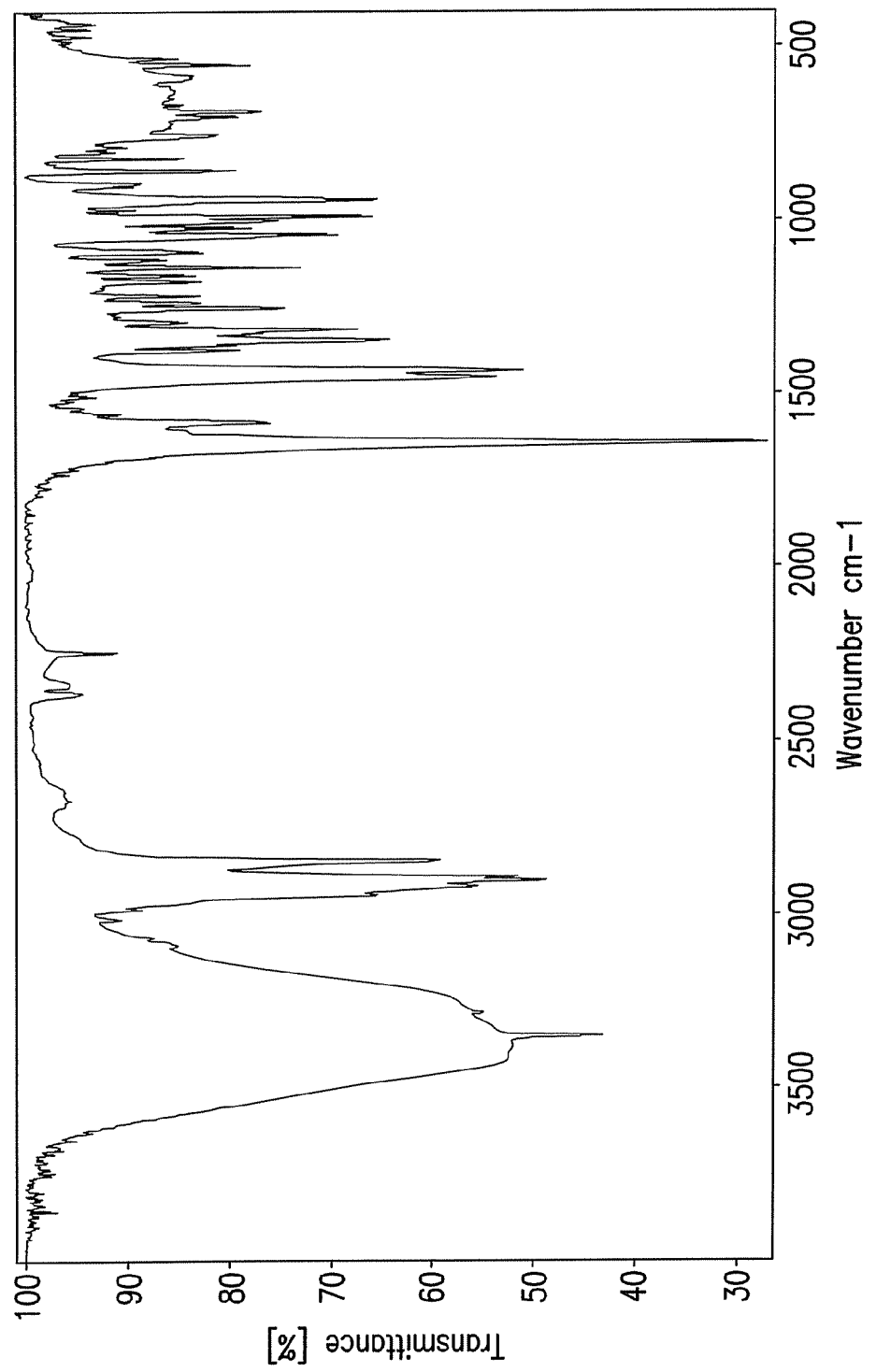
FIG. 15 shows a FT-IR spectrum of crystalline Saxagliptin monohydrate form H-1.

As used herein, the term crystalline Saxagliptin monohydrate form H-1 refers to a crystalline Saxagliptin characterized by suitable analytical data. Suitable analytical data may include, for example: a powder XRD pattern having peaks at 12.4, 13.3, 13.6, 14.7, 16.2, 18.2, 19.9, 20.9, 21.9 and 22.4 degrees 2-theta±0.1 degrees 2-theta, a PXRD pattern substantially as depicted in FIG. 14, a FTIR pattern substantially as depicted in FIG. 15, or combinations of these analytical data.

As used herein, the expression "Room temperature" refers to a temperature between about 20° C. and about 30° C. Usually, room temperature ranges from about 20° C. to about 25° C.

As used herein, the term "wet crystalline form" refers to a polymorph that was not dried using any conventional techniques to remove residual solvent. Examples for such conventional techniques include, but are not limited to, evaporation, vacuum drying, oven drying, drying under nitrogen flow etc.

As used herein, the term "dry crystalline form" refers to a polymorph that was dried using any conventional techniques to remove residual solvent. Examples for such conventional techniques include, but are not limited to, evaporation, vacuum drying, oven drying, drying under nitrogen flow etc.

As used herein, the term "wet ethyl acetate" refers to ethyl acetate that was washed with water.

Figure 16:
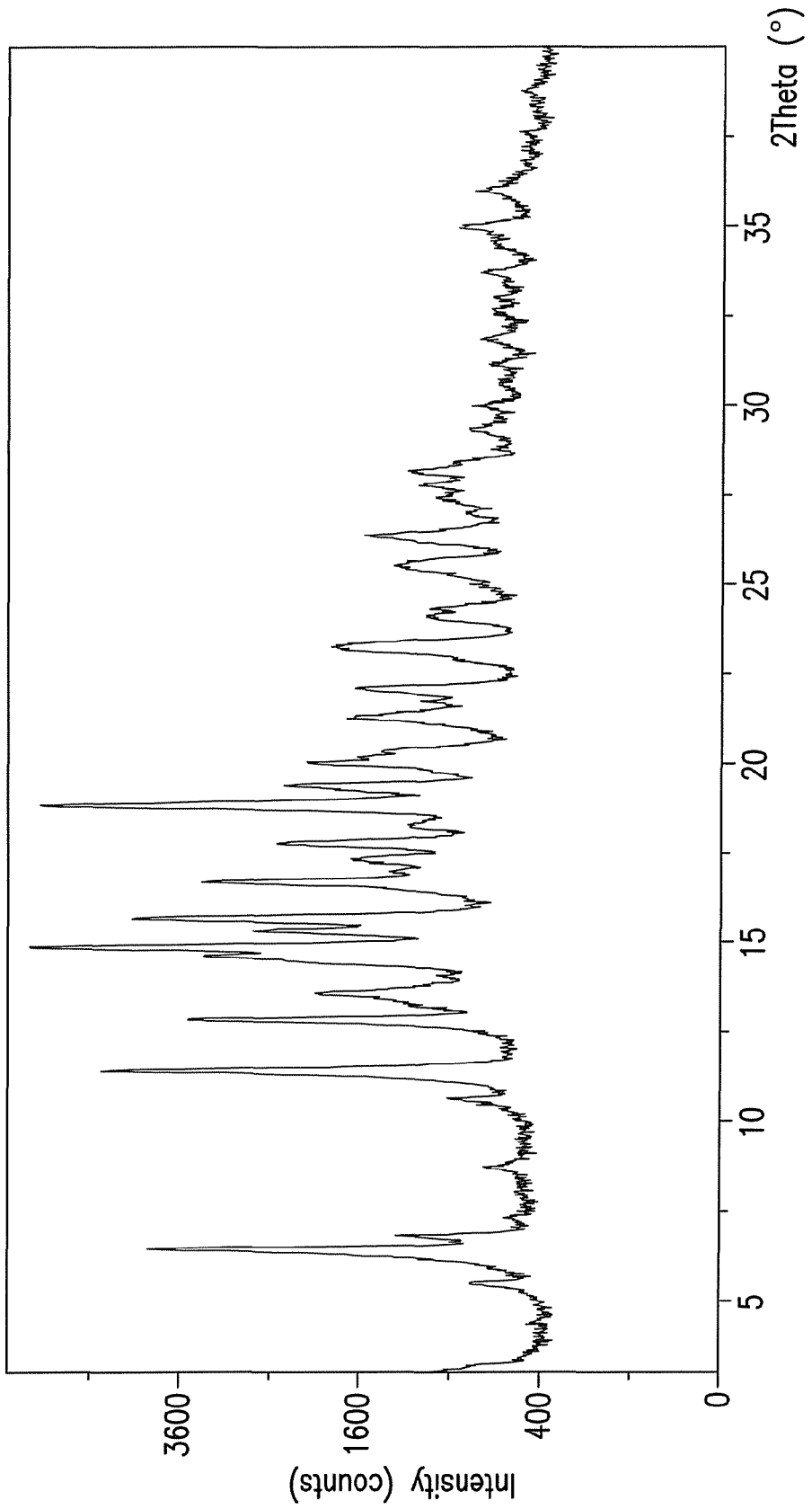
FIG. 16 shows a powder XRD pattern of crystalline Saxagliptin hydrochloride designated form K.
Figure 19:
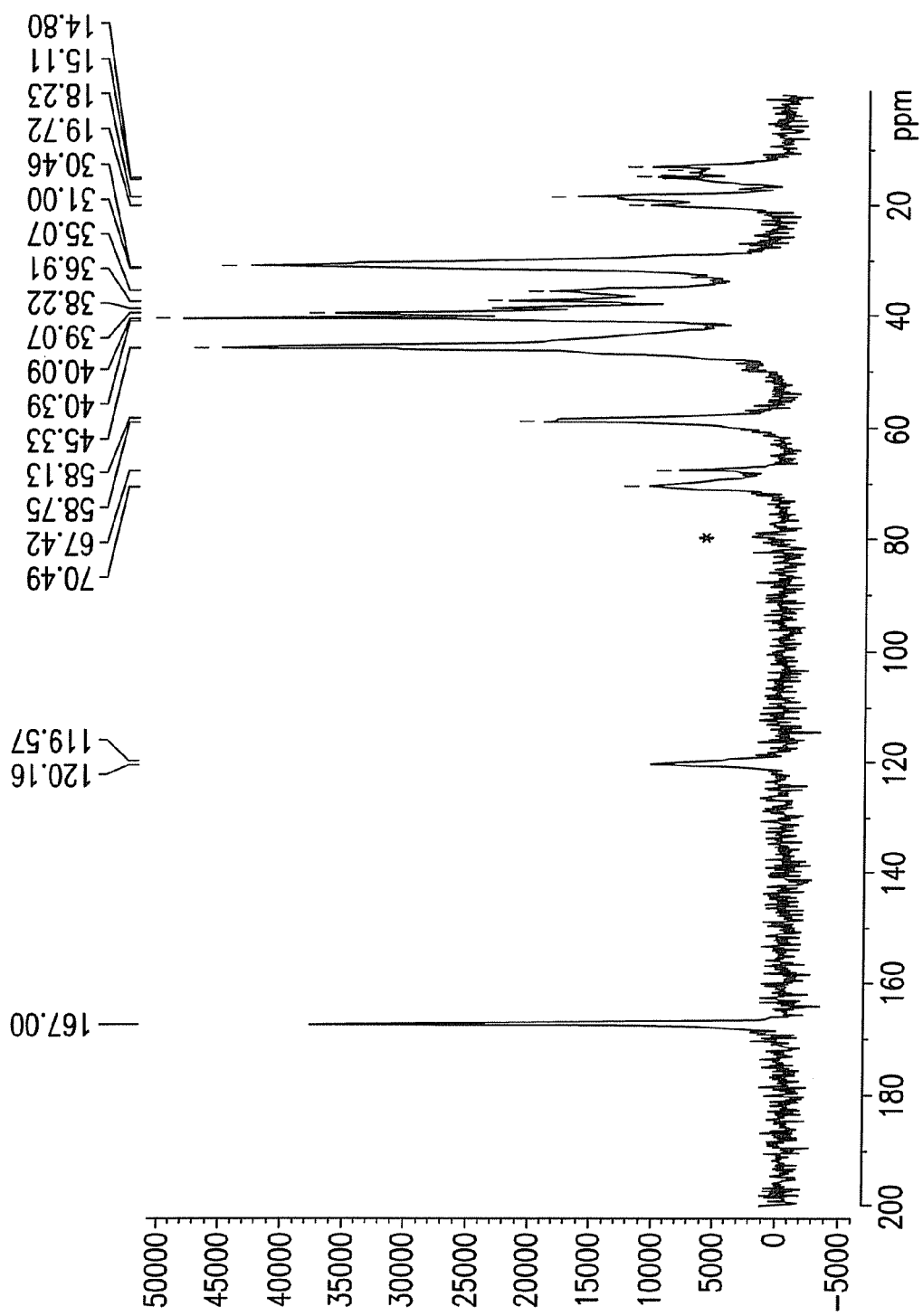
FIG. 19 provides a solid state $^{13}C$ NMR pattern of crystalline Saxagliptin hydrochloride designated form K.

In one embodiment, the invention encompasses crystalline Saxagliptin hydrochloride, designated form K. Form K can be characterized by data selected from: a powder XRD pattern having peaks at 6.4, 11.4, 12.8, 15.7, and 19.4 degrees 2-theta±0.2 degrees 2-theta; an X-ray powder diffraction pattern substantially as depicted in FIG. 16; a solid-state $^{13}$C NMR spectrum having characteristic peaks at 167.0, 120.2, 58.8, 45.3 and 30.5 ppm,±0.2 ppm; a solid-state $^{13}$C NMR spectrum substantially as depicted in FIG. 19; and combinations thereof.

Form K can be further characterized by additional powder XRD peaks at 5.4, 14.8, 16.7, and 22.1 degrees 2-theta±0.2 degrees 2-theta.

Alternatively Saxagliptin hydrochloride form K can be characterized by a powder XRD pattern with peaks at 6.4, 11.4, 12.8, 15.7, and 19.4 degrees two theta±0.2 degrees two theta; and also having one, two, three, or four peaks selected from 5.4, 14.8, 16.7, and 22.1 degrees two theta±0.2 degrees two theta.

The above form K can be a hydrate. Typically, the water content in the crystalline Saxagliptin hydrochloride form K is about 8% (w/w, as measured by TGA at temperature between about room temperature to about 150° C.)

The crystalline Saxagliptin hydrochloride form K of the present invention has advantageous properties selected from at least one of: chemical purity, flowability, solubility, morphology or crystal habit, stability—such as storage stability, stability to dehydration, stability to polymorphic conversion, low hygroscopicity, low content of residual solvents.

Particularly, the crystalline Saxagliptin hydrochloride form K of the present invention exhibits high tapped density, of about 0.32 g/ml in comparison to crystalline Saxagliptin hydrochloride form H2-1 which exhibits tapped density of about 0.28 g/ml. The high tapped density can be advantageous during formulation, in particular it is advantageous for tablet compression and condensation.

Figure 3:
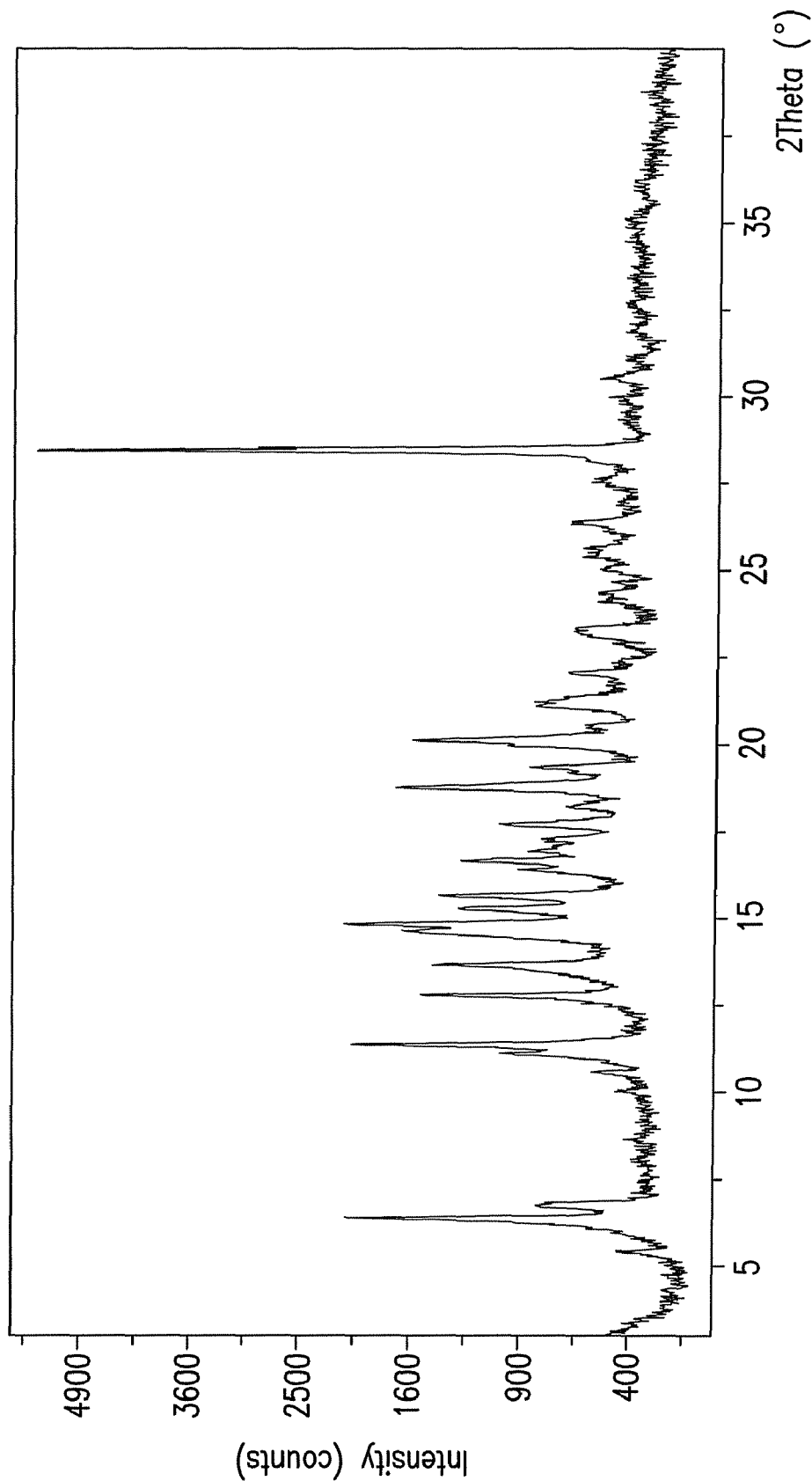
FIG. 3 shows a powder XRD pattern of crystalline Saxagliptin hydrochloride designated form K, in a mixture with crystalline Saxagliptin monohydrochloride dihydrate H2-1.

Saxagliptin hydrochloride Form K can be in a mixture with crystalline Saxagliptin monohydrochloride dihydrate form H2-1. This mixture can be characterized by a powder XRD pattern substantially as depicted in FIG. 3.

Typically, the presence of Saxagliptin monohydrochloride dihydrate form H2-1 in the mixture can be can be detected by PXRD using the peaks at 11.1, 13.7, and 20.1 degrees two theta±0.2 degrees two theta (corrected according to Si position at 28.44° 2θ).

Form K is preferably polymorphically pure. The expression "polymorphically pure" as used herein means that the crystal form is substantially free of any other crystalline (or polymorphic) forms, as described above.

In particular, form K is substantially free of crystalline Saxagliptin hydrochloride form H2-1, characterized above; and crystalline Saxagliptin hydrochloride form O, characterized hereinafter.

In another embodiment, the invention encompasses crystalline Saxagliptin hydrochloride, designated foam T. Form T can be characterized by a powder XRD pattern having peaks at 8.6, 14.3, 15.1, 17.5, and 22.6 degrees 2-theta±0.2 degrees 2-theta. Form T can be further characterized by additional powder XRD peaks at 17.2, 18.5, and 19.2 degrees 2-theta±0.2 degrees 2-theta.

Alternatively Saxagliptin hydrochloride form T can be characterized by a powder XRD pattern with peaks at 8.6, 14.3, 15.1, 17.5, and 22.6 degrees two theta±0.2 degrees two theta; and also having one, two or three peaks selected from 17.2, 18.5, and 19.2 degrees two theta±0.2 degrees two theta.

Figure 4:
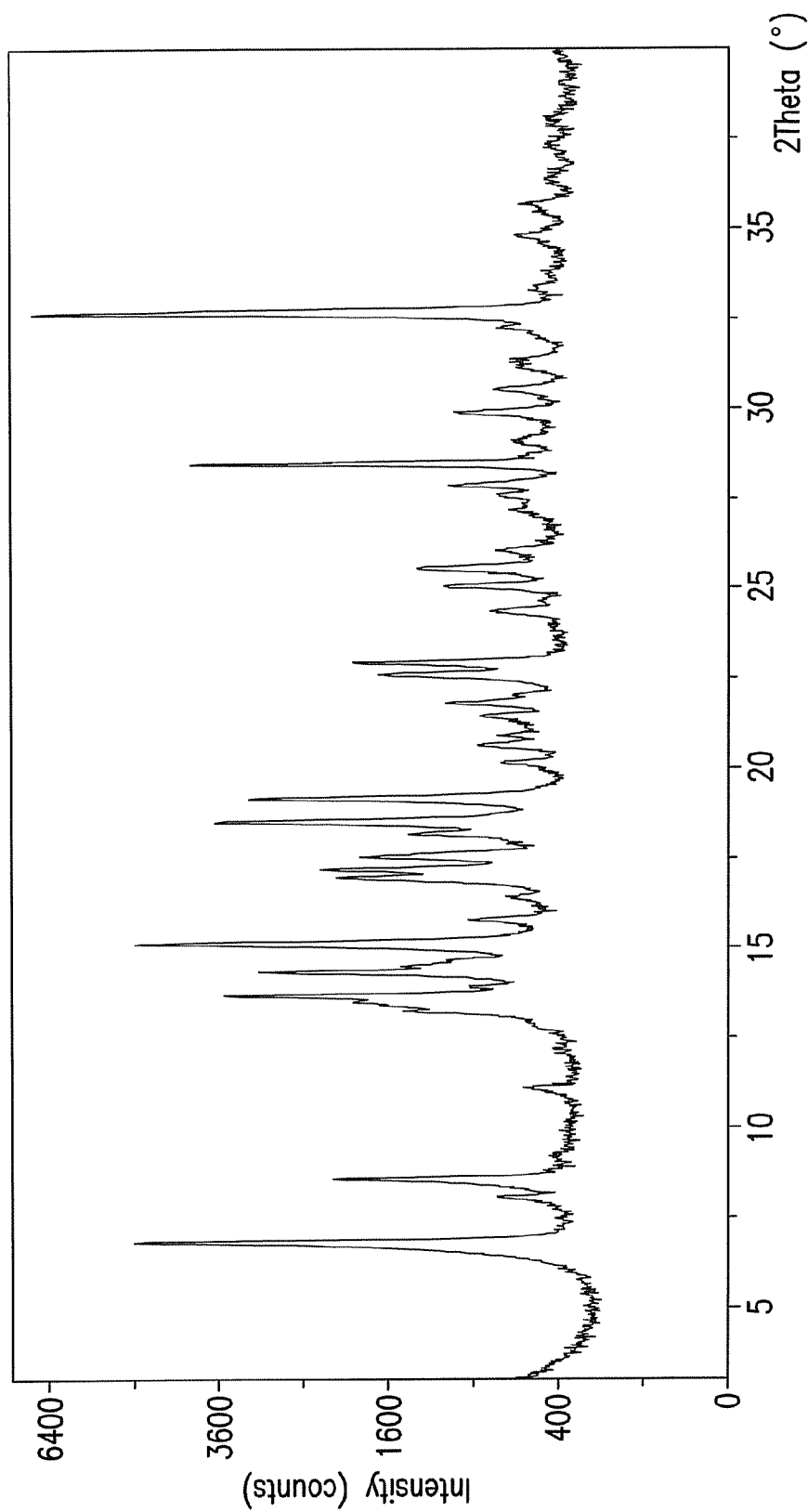
FIG. 4 shows a powder XRD pattern of crystalline Saxagliptin hydrochloride designated form T, in a mixture with ammonium chloride.

Saxagliptin hydrochloride Form T can be in a mixture with ammonium chloride. This mixture can be characterized by a powder XRD pattern substantially as depicted in FIG. 4. Typically, the presence of ammonium chloride in the mixture can be can be detected by PXRD using the peaks at 22.9 and 32.7 degrees two theta±0.2 degrees two theta. In addition, the presence and quantity of any ammonium chloride present in Saxagliptin hydrochloride Form T may be analyzed by any other suitable analytical method, for example ion chromatography or CHN elemental analysis.

Figure 18:
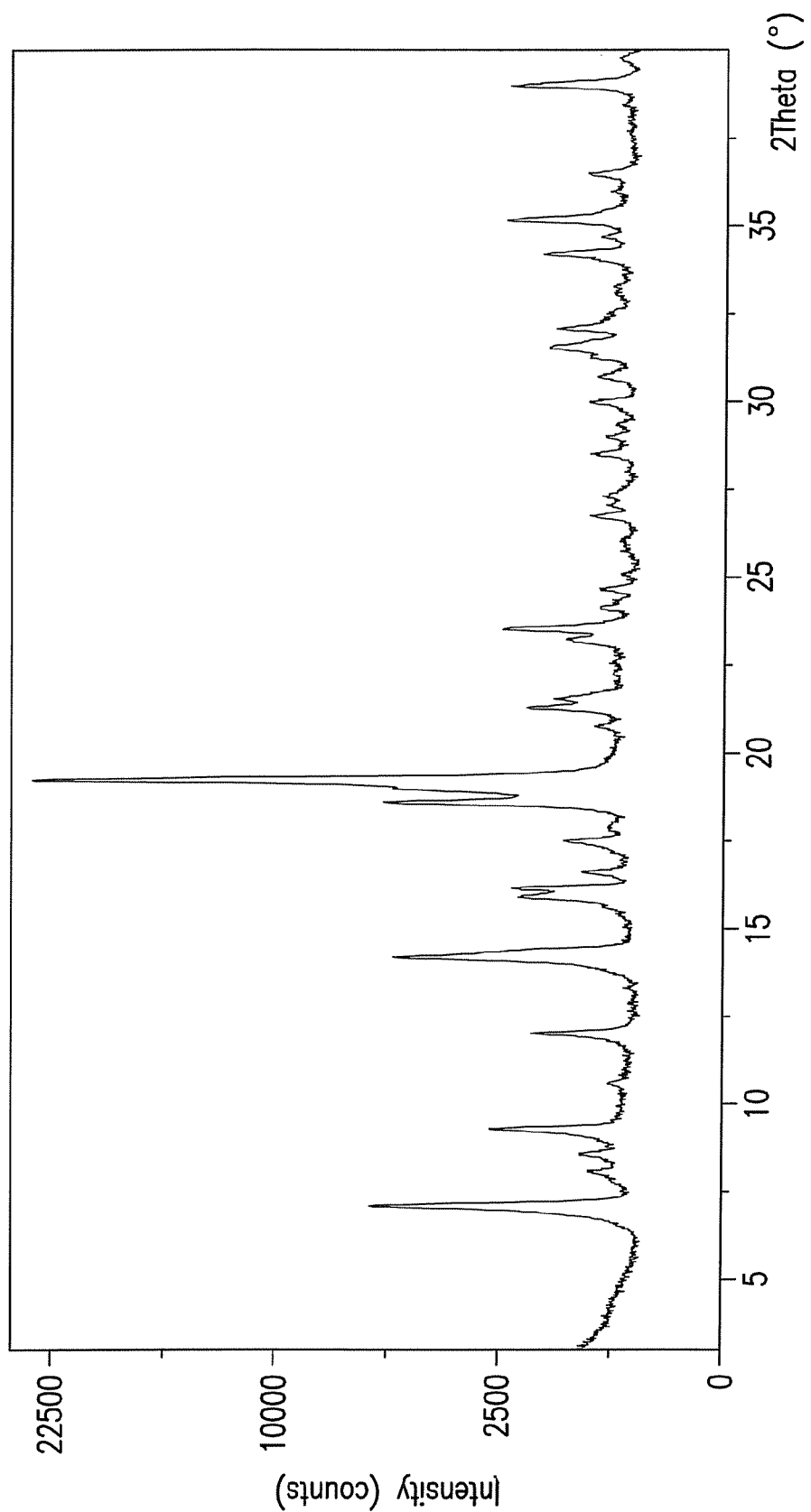
FIG. 18 shows a powder XRD pattern of crystalline Saxagliptin hydrochloride designated form Z.
Figure 20:
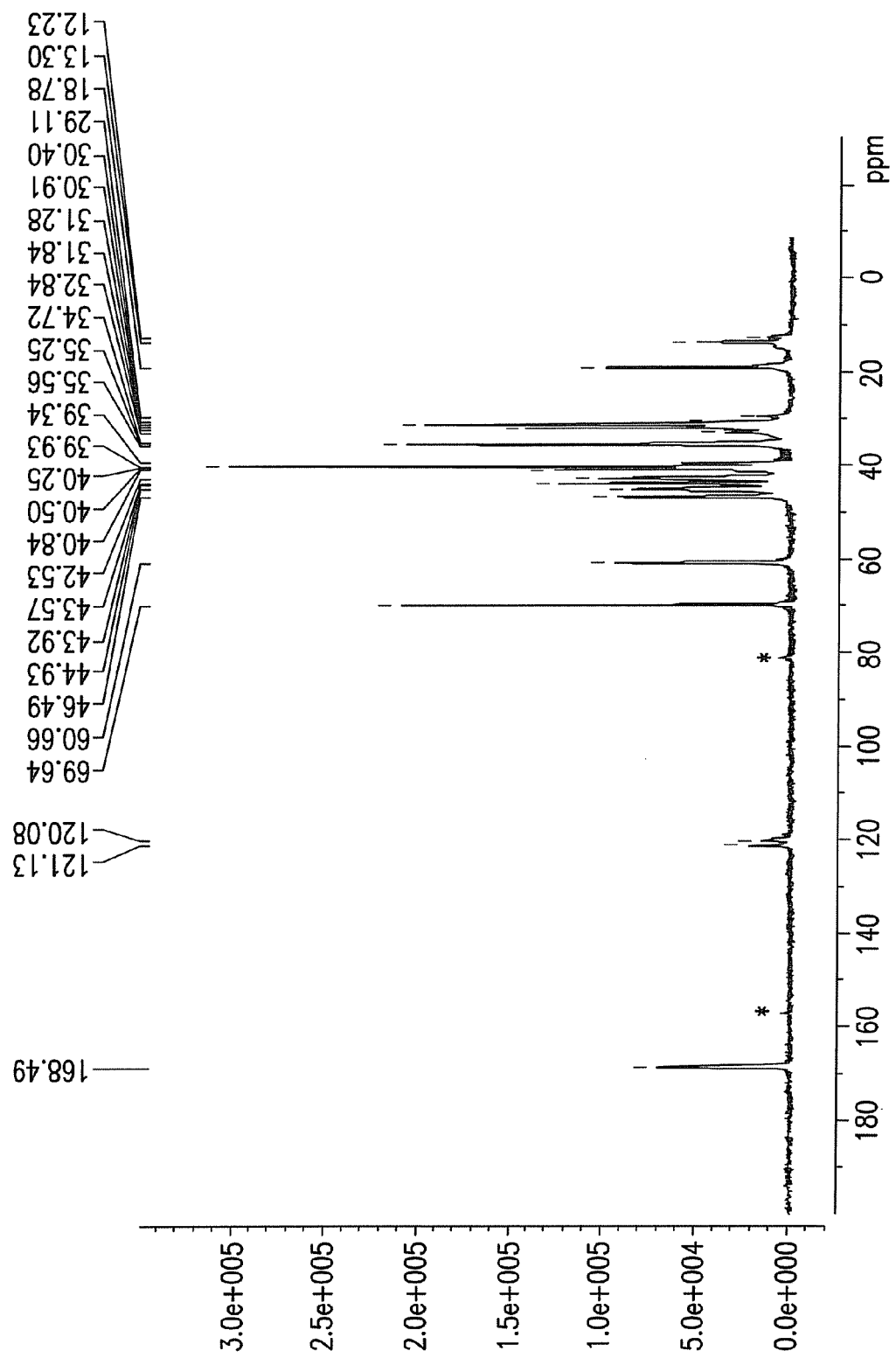
FIG. 20 provides a solid state $^{13}C$ NMR pattern of crystalline Saxagliptin hydrochloride designated form Z.
Figure 21:
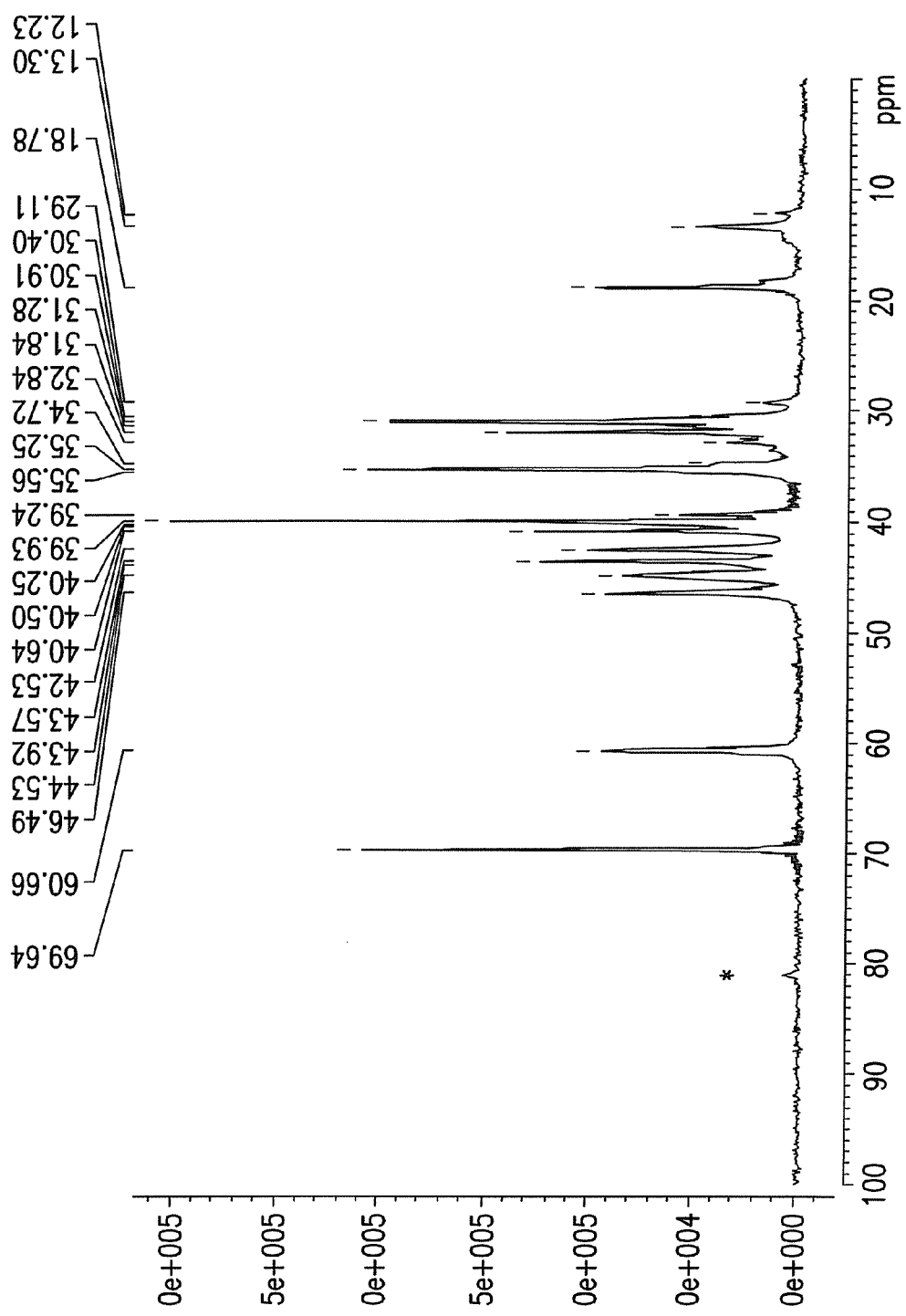
FIG. 21 provides a detailed solid state $^{13}C$ NMR pattern of crystalline Saxagliptin hydrochloride designated form Z in range 100-0 ppm.

In another embodiment, the invention encompasses crystalline Saxagliptin hydrochloride, designated form Z. Saxagliptin hydrochloride form Z can be characterized by data selected from: an X-ray powder diffraction pattern having peaks at 9.3, 12.0, 14.2 and 19.2 degrees two theta±0.2 degrees two theta; an X-ray powder diffraction pattern substantially as depicted in FIG. 18; a solid-state $^{13}$C NMR spectrum having characteristic peaks at 46.5, 44.9, 42.5 and 29.1 ppm,±0.1 ppm; a solid-state $^{13}$C NMR spectrum substantially as depicted in any one of FIGS. 20-21; and combinations thereof.

The Saxagliptin hydrochloride form Z may be further characterized by an X-ray powder diffraction pattern having additional peaks at 8.1, 16.6 and 23.2 degrees two theta±0.2 degrees two theta; and combinations thereof.

The above form Z can be a hydrate. Typically, the water content in the crystalline Saxagliptin hydrochloride foam Z is about 6.5% (w/w, as measured by TGA at temperature between about room temperature to about 150° C.)

The crystalline Saxagliptin hydrochloride form Z of the present invention has advantageous properties selected from at least one of: chemical purity, flowability, solubility, morphology or crystal habit, stability—such as storage stability, stability to dehydration, stability to polymorphic conversion, low hygroscopicity, low content of residual solvents.

Particularly, the crystalline Saxagliptin hydrochloride form Z of the present invention exhibits high dissolution rate, and therefore has enhanced dissolution rate as compared to other solid state forms of Saxagliptin hydrochloride.

The above form Z can be polymorphically pure. The expression "polymorphically pure" as used herein means that the crystal form is substantially free of any other crystalline (or polymorphic) forms, as described above. In particular, form Z is substantially free of crystalline Saxagliptin hydrochloride form D, characterized hereinafter.

Typically, the amount of crystalline Saxagliptin hydrochloride form D in the crystalline Saxagliptin hydrochloride form Z of the present invention can be measured by PXRD using the peaks at 15.4, 18.9, and 22.6 degrees 2-theta±0.2 degrees 2-theta to quantify the amount of form Z.

Figure 5:
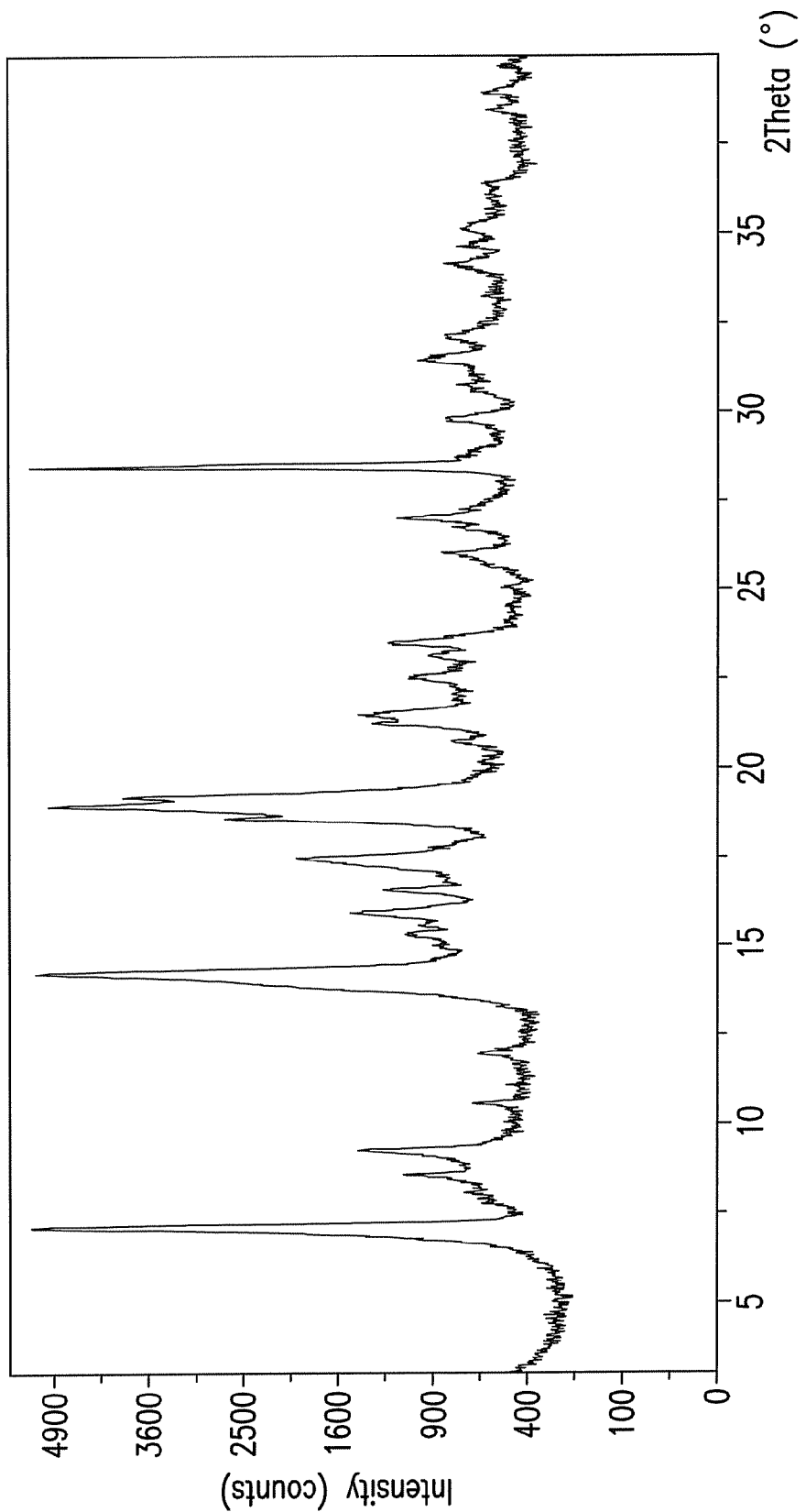
FIG. 5 shows a powder XRD pattern of crystalline Saxagliptin hydrochloride designated form Z in a mixture with form D.
Figure 12:
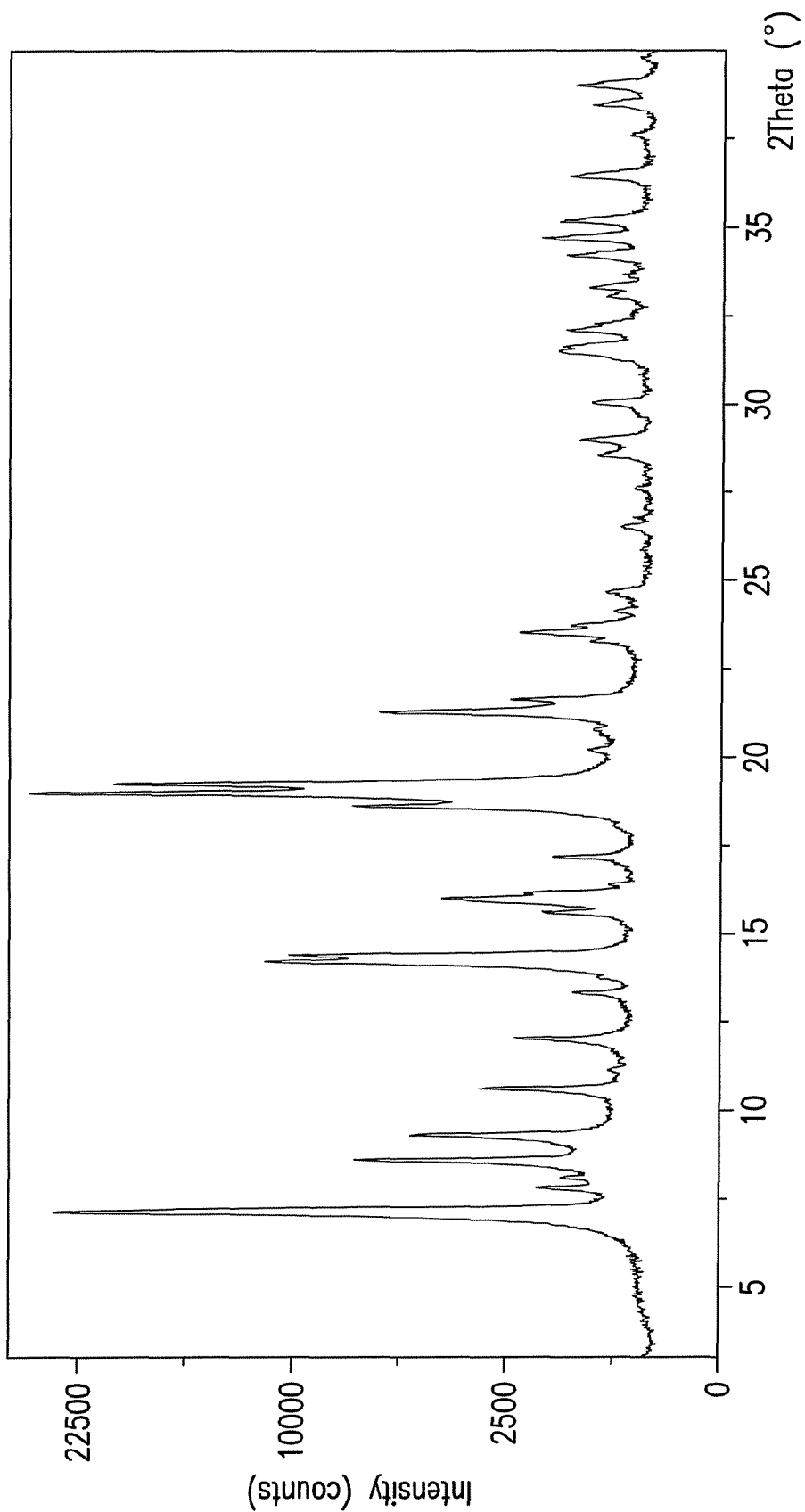
FIG. 12 shows a powder XRD pattern of crystalline Saxagliptin hydrochloride designated form Z in a mixture with form D.

The invention also provides a mixture of crystalline Saxagliptin hydrochloride, form Z and of crystalline Saxagliptin hydrochloride form D. The mixture can be characterized by data selected from: an X-ray powder diffraction pattern having peaks at 7.1, 9.3, 15.9, 18.9, and 23.5 degrees two theta±0.2 degrees two theta; an X-ray powder diffraction pattern having peaks at 7.1, 9.3, 15.9, 19.0, and 23.5 degrees two theta±0.2 degrees two theta; an X-ray powder diffraction pattern substantially as depicted in FIG. 5; an X-ray powder diffraction pattern substantially as depicted in FIG. 12; and combinations thereof. The mixture may be further characterized by an X-ray powder diffraction pattern having additional peaks at 14.3, 17.5, and 19.2 degrees two theta±0.2 degrees two theta.

The mixture can be characterized by any combination of the above data.

Figure 6:
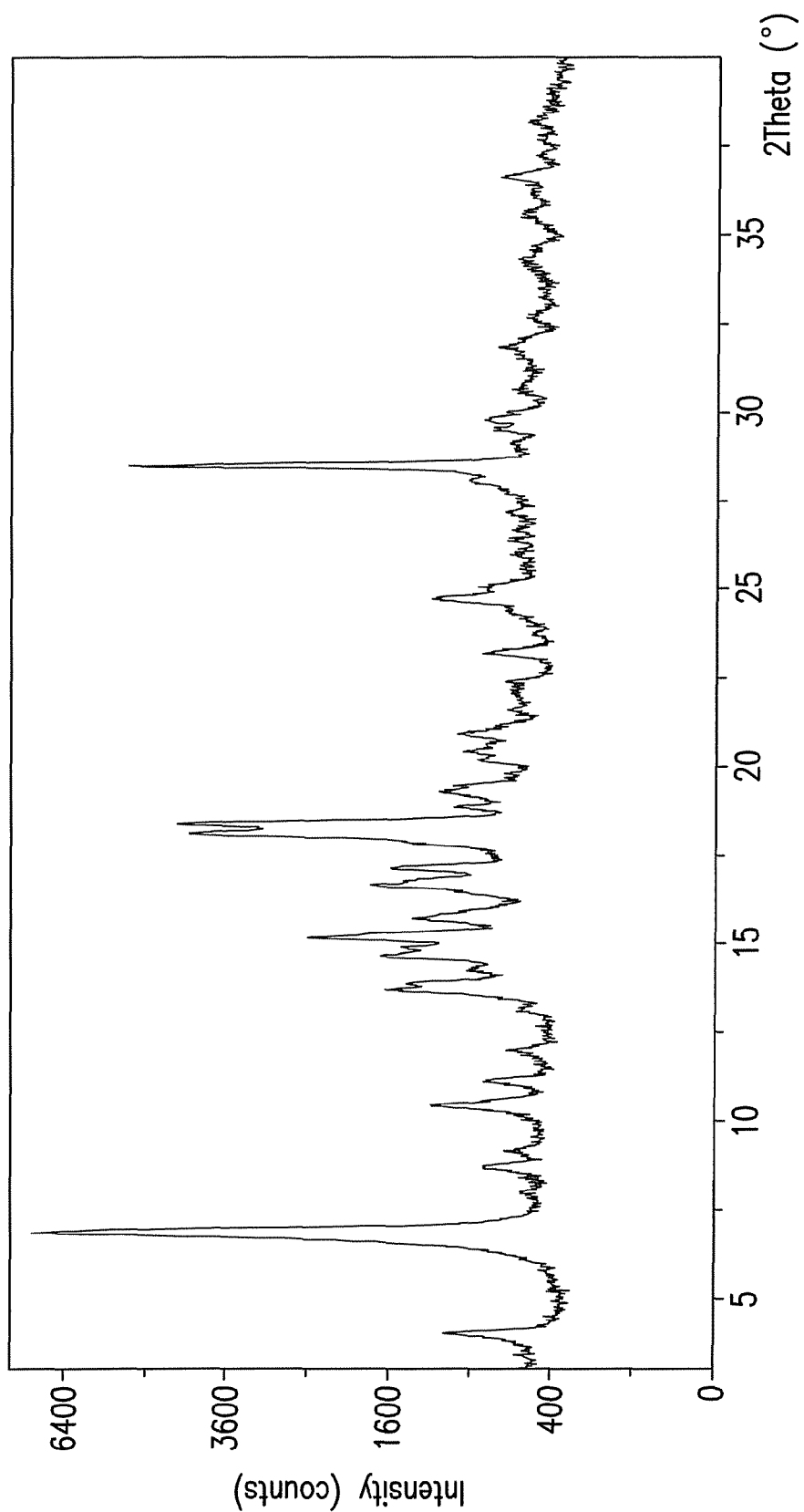
FIG. 6 shows a powder XRD pattern of crystalline Saxagliptin hydrochloride designated form N.

In another embodiment, the invention encompasses crystalline Saxagliptin hydrochloride, designated form N. Saxagliptin hydrochloride form N can be characterized by data selected from: an X-ray powder diffraction pattern having peaks at 4.0, 13.9, 17.1 and 18.4 degrees two theta±0.2 degrees two theta; an X-ray powder diffraction pattern substantially as depicted in FIG. 6; and combinations thereof.

Figure 7:
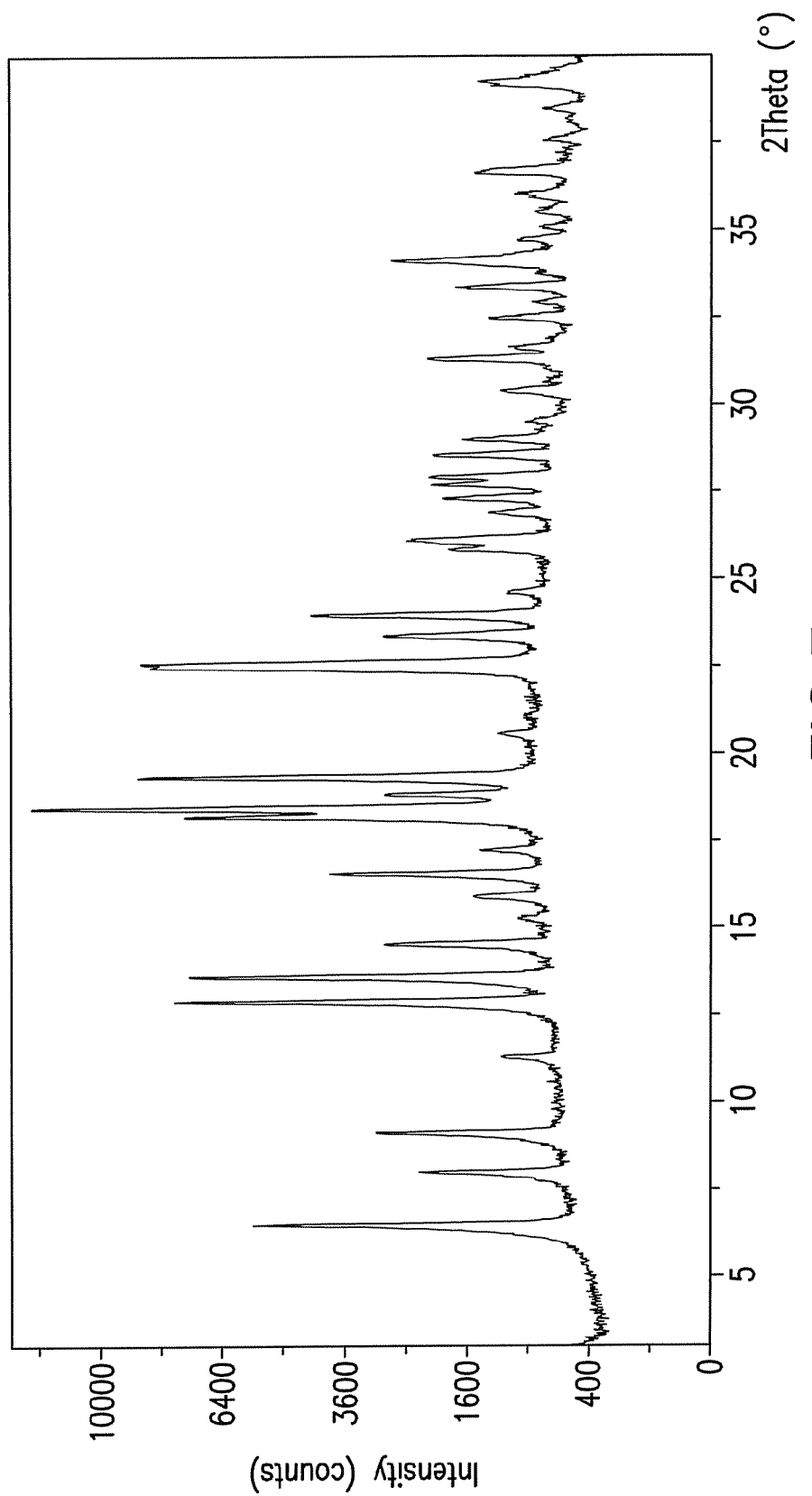
FIG. 7 shows a powder XRD pattern of crystalline Saxagliptin hydrochloride designated form S.

In another embodiment, the invention encompasses crystalline Saxagliptin hydrochloride, designated form S. Saxagliptin hydrochloride form S can be characterized by data selected from: an X-ray powder diffraction pattern having peaks at 8.0, 9.1, 12.9, 18.4 and 24.0 degrees two theta±0.2 degrees two theta; an X-ray powder diffraction pattern substantially as depicted in FIG. 7; and combinations thereof.

In one embodiment, the invention encompasses crystalline Saxagliptin hydrochloride, designated form O. Form O can be characterized by a powder XRD pattern having peaks at 5.6, 9.1, 13.1 and 19.7 degrees 2-theta±0.2 degrees 2-theta.

Figure 8:
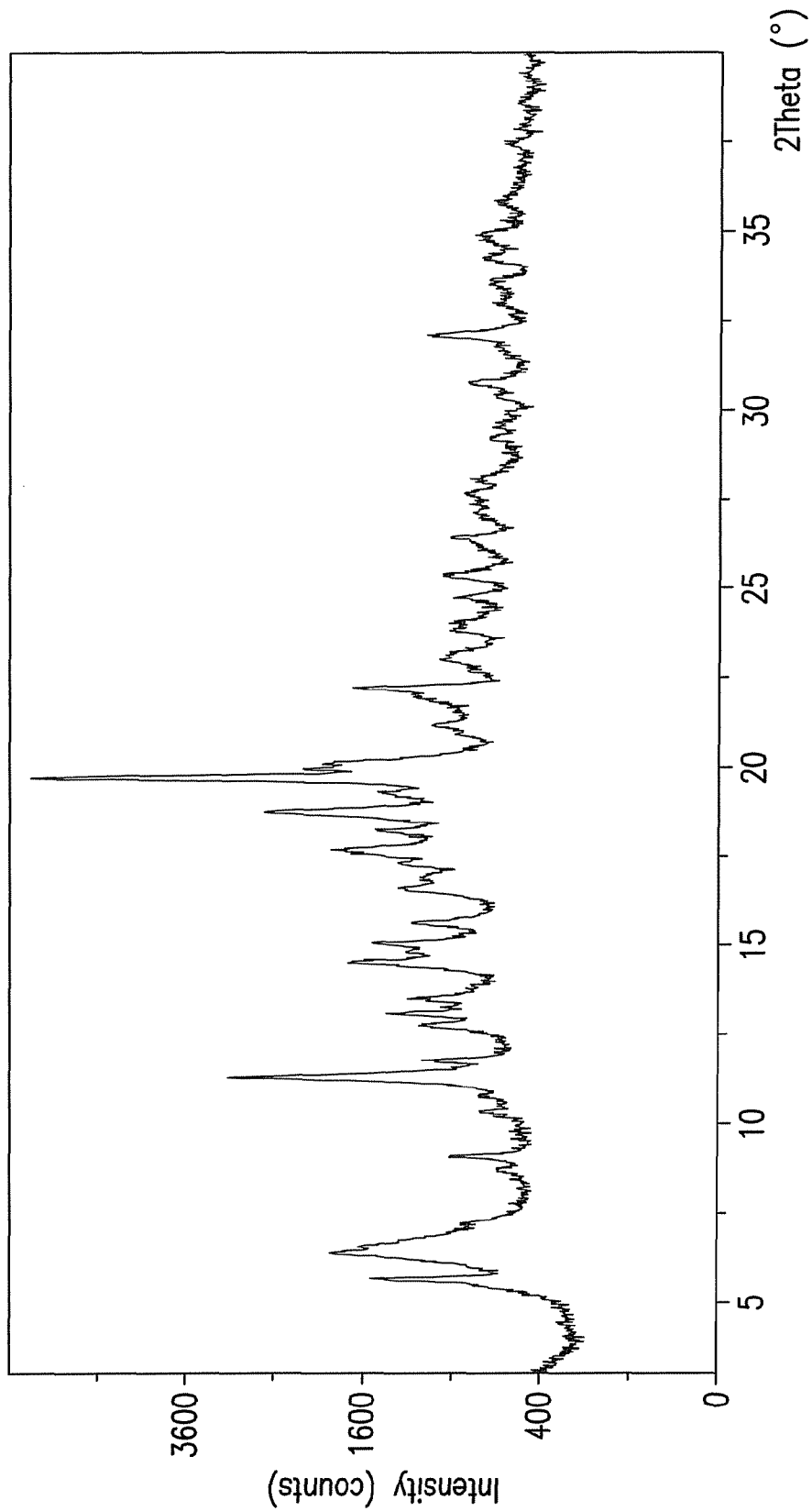
FIG. 8 shows a powder XRD pattern of crystalline Saxagliptin hydrochloride designated form O, in a mixture with crystalline Saxagliptin hydrochloride K.

Saxagliptin hydrochloride Form 0 can be in a mixture with crystalline Saxagliptin monohydrochloride dihydrate form K. This mixture can be characterized by a powder XRD pattern substantially as depicted in FIG. 8. Typically, the presence of Saxagliptin monohydrochloride form K in the mixture can be can be detected by PXRD using the peaks at 6.3 and 12.7 degrees two theta±0.2 degrees two theta.

In one embodiment, the invention encompasses crystalline Saxagliptin hydrochloride, designated form B. Form B can be characterized by a powder XRD pattern having peaks at 5.9, 6.5, 17.8 and 20.5 degrees 2-theta±0.2 degrees 2-theta.

Figure 9:
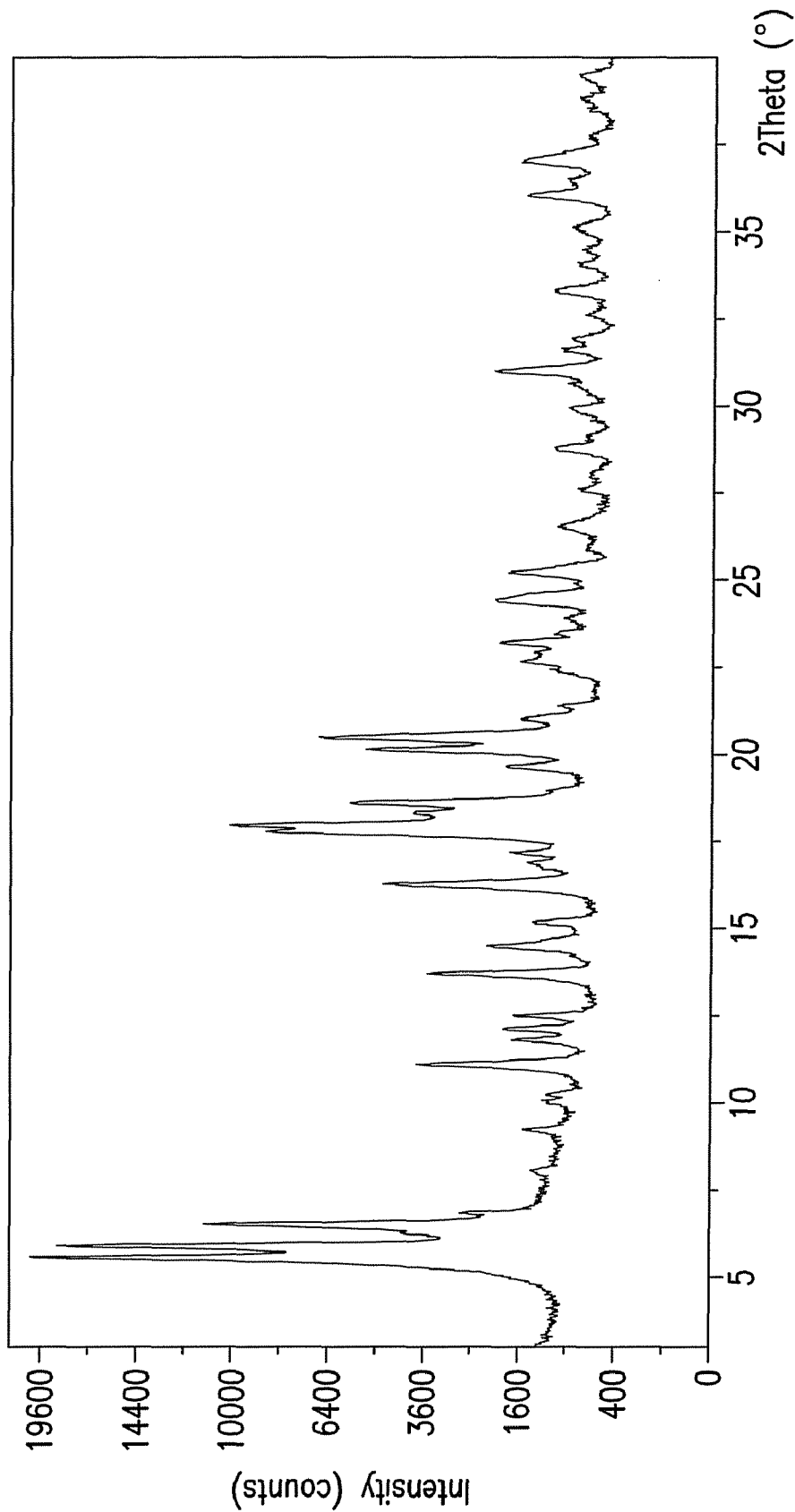
FIG. 9 shows a powder XRD pattern of crystalline Saxagliptin hydrochloride designated form B, in a mixture with crystalline Saxagliptin monohydrochloride dihydrate H2-1.

Saxagliptin hydrochloride Form B can be in a mixture with crystalline Saxagliptin monohydrochloride dihydrate form H2-1. This mixture can be characterized by a powder XRD pattern substantially as depicted in FIG. 9. Typically, the presence of Saxagliptin monohydrochloride dihydrate form H2-1 in the mixture can be can be detected by PXRD using the peaks at 11.1, 13.7 and 20.1 degrees two theta±0.2 degrees two theta.

Figure 10:
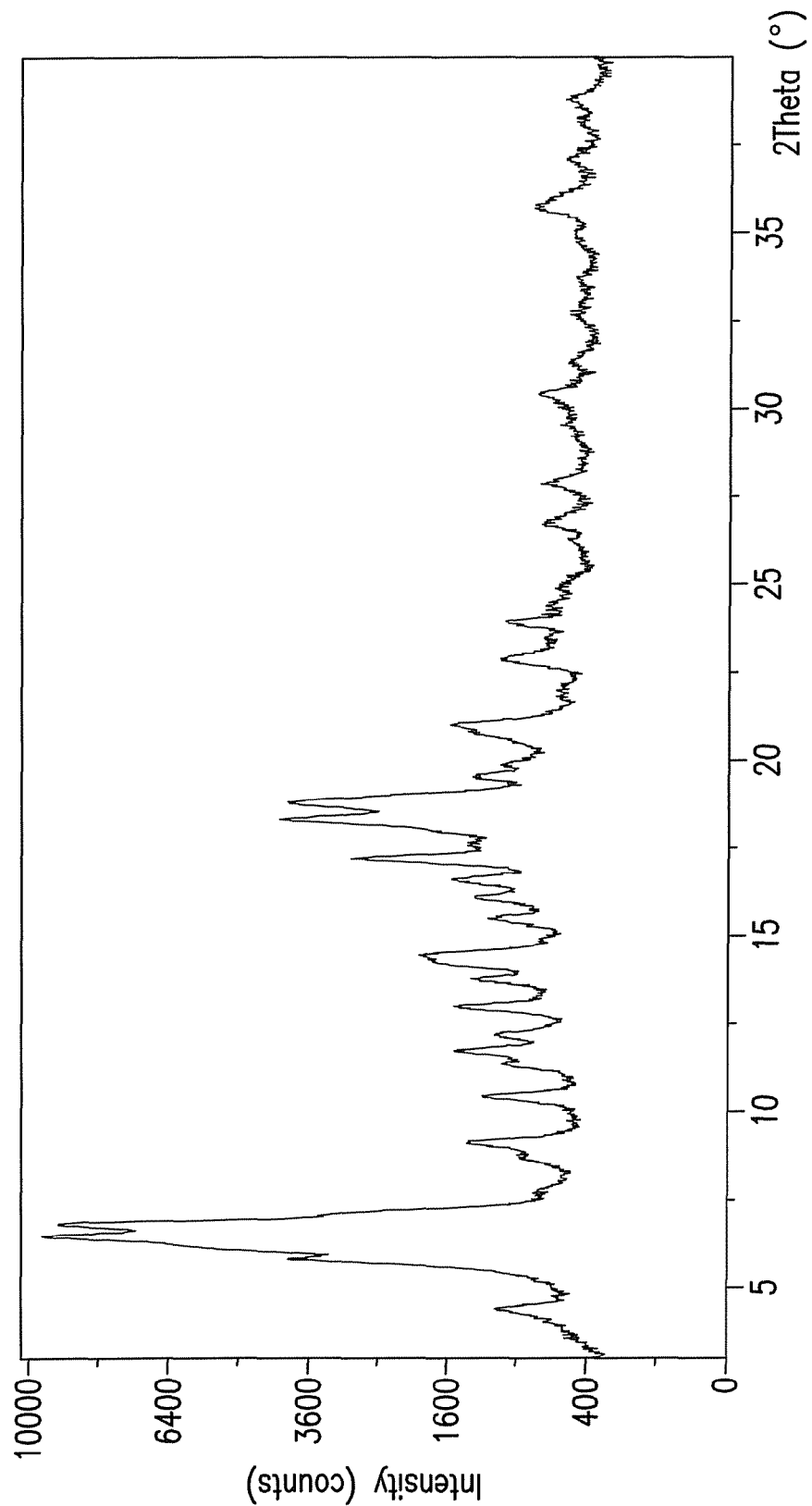
FIG. 10 shows a powder XRD pattern of crystalline Saxagliptin hydrochloride designated form C.

In another embodiment; the invention encompasses crystalline Saxagliptin hydrochloride, designated form C. Saxagliptin hydrochloride form C can be characterized by data selected from: an X-ray powder diffraction pattern having peaks at 4.4, 6.9, 17.2 and 18.3 degrees two theta±0.2 degrees two theta; an X-ray powder diffraction pattern substantially as depicted in FIG. 10; and combinations thereof.

Figure 11:
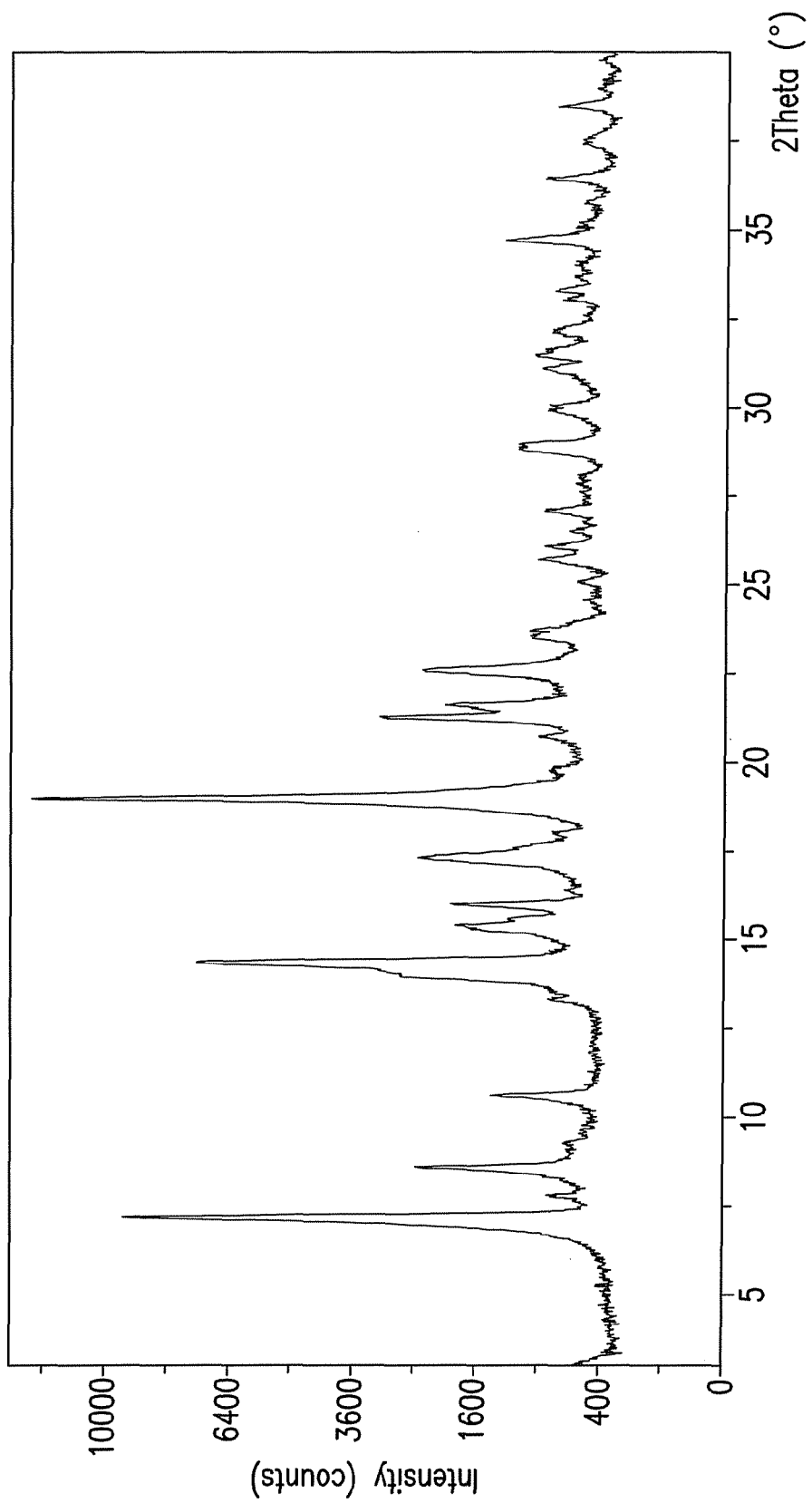
FIG. 11 shows a powder XRD pattern of crystalline Saxagliptin hydrochloride designated form D
Figure 22:
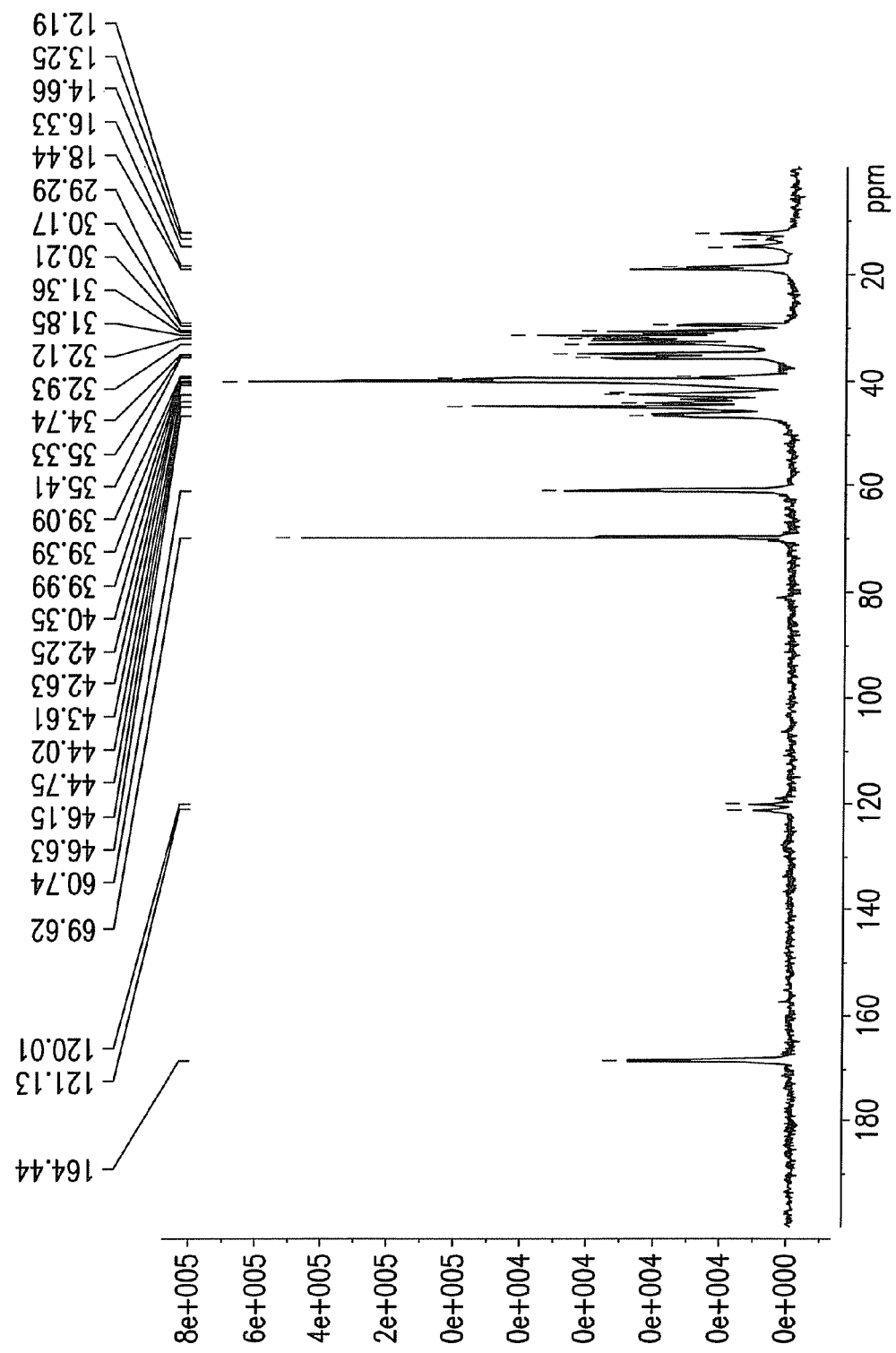
FIG. 22 provides a solid state $^{13}C$ NMR pattern of crystalline Saxagliptin hydrochloride designated form D.
Figure 23:
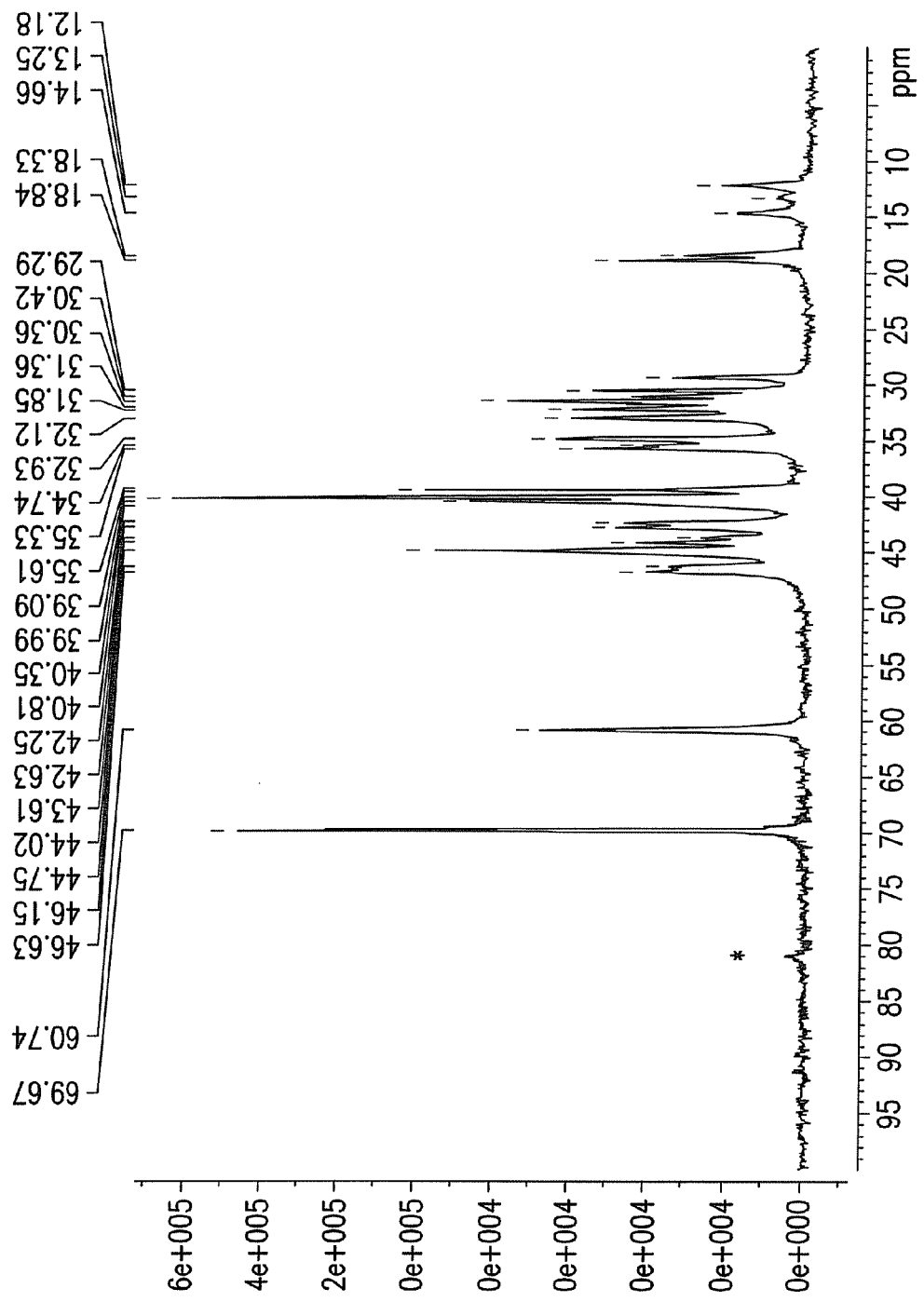
FIG. 23 provides a detailed solid state $^{13}C$ NMR pattern of crystalline Saxagliptin hydrochloride designated form D in range 100-0 ppm.

In yet another embodiment, the invention encompasses crystalline Saxagliptin hydrochloride designated form D. Saxagliptin hydrochloride designated form D can be characterized by data selected from: an X-ray powder diffraction pattern having peaks at 10.6, 14.4, 15.4, 17.3, 22.6 and 25.7 degrees two theta±0.2 degrees two theta; an X-ray powder diffraction pattern substantially as depicted in FIG. 11; and combinations thereof; a solid-state $^{13}C$ NMR spectrum having characteristic peaks at 46.2, 44.8, 42.3, 32.1 and 14.7 ppm,±0.1 ppm; a solid-state $^{13}C$ NMR spectrum substantially as depicted in any one of FIGS. 22 and 23.

The Saxagliptin hydrochloride form D may be further characterized by an X-ray powder diffraction pattern having additional peaks at 8.6 and 19.0 degrees two theta±0.2 degrees two theta.

The above form D can be a hydrate. Typically, the water content in the crystalline Saxagliptin hydrochloride form D is about 6.3% (w/w, as measured by TGA at temperature between about room temperature to about 150° C.)

The crystalline Saxagliptin hydrochloride form D of the present invention has advantageous properties selected from at least one of: chemical purity, flowability, solubility, morphology or crystal habit, stability—such as storage stability, stability to dehydration, stability to polymorphic conversion, low hygroscopicity, low content of residual solvents.

Figure 24:
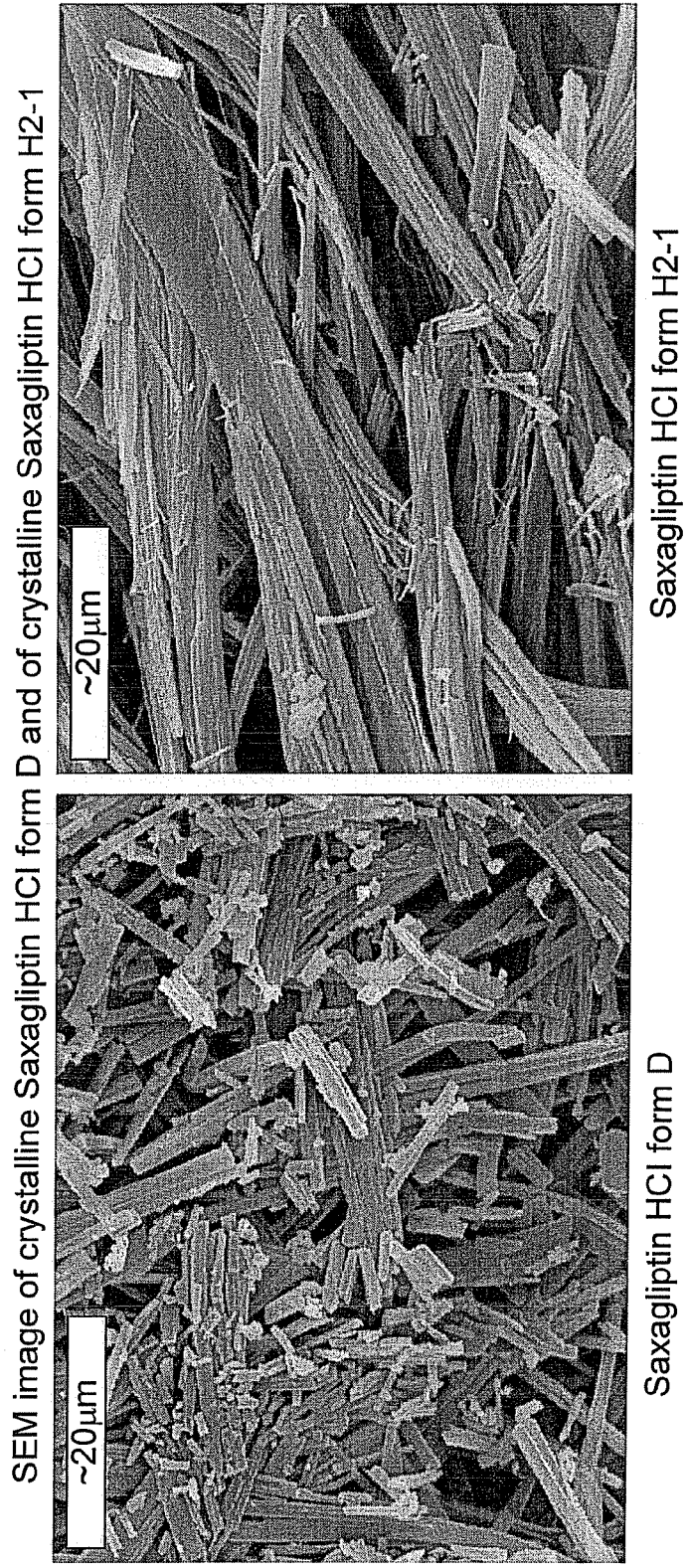
FIG. 24 provides a scanning electron microscope (SEM) image of crystalline Saxagliptin hydrochloride form D and of crystalline Saxagliptin hydrochloride form H2-1.

Particularly, the crystalline Saxagliptin hydrochloride form D of the present invention comprises small plate to rod-shaped particles, exhibits good filterability and powder flowability properties. A SEM image of crystalline Saxagliptin hydrochloride form D and form H2-1 is presented in FIG. 24.

Figure 17:
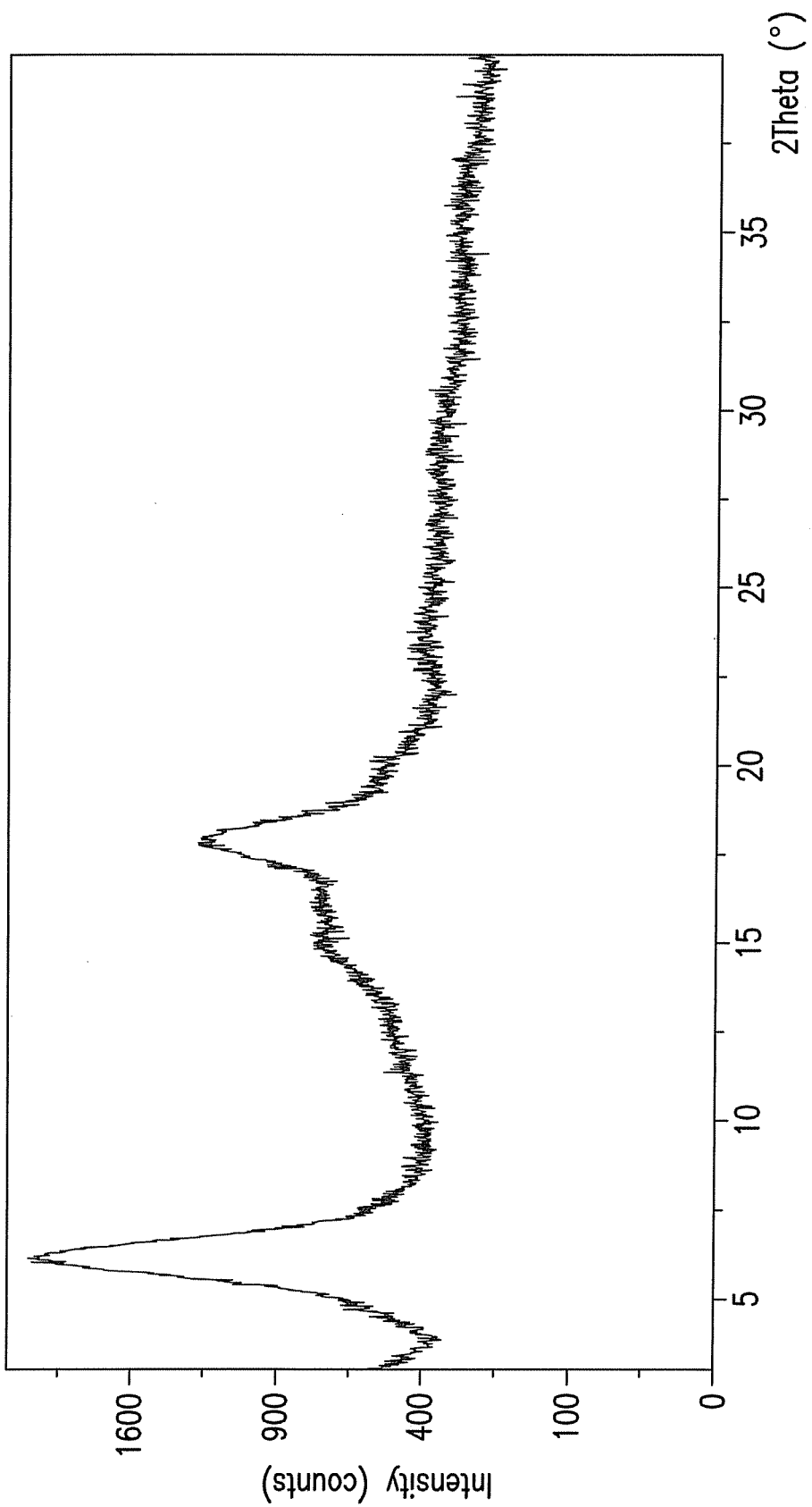
FIG. 17 shows a powder XRD pattern of amorphous Saxagliptin.

The present invention also encompasses amorphous Saxagliptin hydrochloride. The amorphous Saxagliptin hydrochloride can be characterized by an X-ray powder diffraction pattern substantially as depicted in FIG. 17.

The amorphous Saxagliptin hydrochloride can be prepared by a process comprising: (a) providing a solution of Boc-Saxagliptin and hydrochloric acid in dry ethanol or dry iso-propanol; and (b) adding a suitable antisolvent, for example, a solvent selected from methyl iso-butyl ketone ("MIBK"), isopropyl acetate and n-butyl acetate to obtain a mixture from which amorphous Saxagliptin hydrochloride precipitates.

Typically, the solution is provided by dissolving Boc-Saxagliptin in dry ethanol or dry iso-propanol and adding a solution of hydrochloric acid in dry ethanol or dry iso-propanol to obtain a mixture. The obtained solution can be heated, for example to reflux temperature, i.e. about 80° C. The mixture is typically maintained at reflux temperature until a solution is formed, typically for a period such as from about 2 hours to about 4 hours. An additional amount of hydrochloric acid in dry ethanolic or iso-propanol solution can than be added during this time.

The solution of Boc-Saxagliptin and hydrochloric acid in dry ethanol is then combined with an anti solvent, typically by adding an anti solvent to the solution. The anti solvent used may be selected from Methyl isobutyl ketone ("MIBK"), isopropyl acetate and n-butyl acetate. The obtained mixture can optionally be cooled to a suitable temperature to aid in precipitation. A suitable cooling temperature can be about room temperature, typically about 20° C. The obtained mixture can be maintained, for example at a temperature from about 0° C. to about 20° C., for a period such as from about 1 hour to about 20 hours, preferably from about 1 hour to about 18 hours, during which time amorphous Saxagliptin hydrochloride precipitates. Typically, it can be maintained for a period from about 1 hour to about 6 hours.

The amorphous Saxagliptin hydrochloride can then be recovered from the mixture. The recovery can comprise, for example, filtering and drying. Drying is typically done under vacuum, with heating, for example to a temperature of about 40° C., for a suitable time, for example about 2 hours.

The above described solid state forms of Saxagliptin hydrochloride can be used to prepare Saxagliptin free base and solid state forms thereof, as well as other solid state forms of Saxagliptin hydrochloride, such as monohydrate form H-1, hemihydrate form H0.5-2, dihydrate form H2-1 and anhydrous form N-3.

The above described solid state forms of Saxagliptin hydrochloride can also be used to prepare pharmaceutical compositions.

The present invention further encompasses 1) a pharmaceutical composition comprising any one or combination of solid state Forms, as described above, and at least one pharmaceutically acceptable excipient; and 2) the use of any one or combination of the above-described solid state Forms, in the manufacture of a pharmaceutical composition, and 3) a method of treating a patient suffering from type 2 diabetes comprising administering one or more of the solid state forms of Saxagliptin hydrochloride or a pharmaceutical composition containing said forms as described herein, in an effective dose or dosage regimen. The pharmaceutical composition can be useful for the treatment of type 2 diabetes. The present invention also provides crystalline forms as described above for use as a medicament, preferably for the treatment of type 2 diabetes.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Powder X-ray Diffraction (PXRD) Method

After being powdered using a mortar and pestle, the sample was applied directly on a silicon plate holder. The X-ray powder diffraction pattern was measured with a Philips X'Pert PRO X-ray powder diffractometer, equipped with a Cu irradiation source=1.54184 Å (Ångstrom), X'Celerator (2.022° 2Θ) detector. Scanning parameters: angle range: 3-40 deg., step size 0.0167, time per step 37 s, continuous scan. The described peak positions of all Saxagliptin hydrochloride crystalline forms of the present invention, except for forms S, O, B, C, pure form Z and D were determined using silicon powder as an internal standard in an admixture with the sample measured. The position of the silicon (Si) peak was corrected to silicone theoretical peak: 28.45 degrees two theta, and the positions of the measured peaks were corrected respectively. No correction was performed on the diffractogram depicted in the figures.

DSC Method

DSC analysis was performed on Q 2000 MDSC TA instruments with a heating rate of 10° C./min, under a nitrogen flow of 50 ml/min. A hermetic aluminium, closed pan with hole was used, and the sample mass was about 1-5 mg.

Solid-State $^{13}$C NMR Method

Solid-state $^{13}$C NMR spectra were recorded with variable amplitude cross polarization, magic angle spinning and high power proton decoupling using a BRUKER Avance II+ spectrometer operating at 125 MHz and ambient temperature (about 25° C.—not controlled). A probe using 4 mm o.d. zirconia rotors was employed. The operation conditions were: contact time: 2 ms; recycle delay: 25 s 256 scans; spin rate of 11 kHz. Chemical shifts were referenced via a replacement sample of glycine (carboxyl carbon chemical shift assigned as 176.03 ppm relative to the signal of tetramethylsilane).

SEM Measurement

Equipment: Jeol JSM-5800 scanning microscope, Sputtered with gold by Edwards S150 sputter coater Tapped Density Measurement:

Equal mass of samples of Forms K and H2-1 (450 mg) of comparable particle size and morphology (comparison analysis based on microscope and SEM images) was weighed in identical graduated cylinders (10 ml measuring flasks). Samples were tapped the same number of times (200 times) with equal force. Volume of each sample was recorded: (1.4 ml for Form K; 1.6 ml for H2-1).

Solubility Measurement

Equal mass of samples was suspended in equal volume of distilled water. Suspensions were slightly mixed, time was recorded at the moment of clear solution appearance.

TGA Method

Equipment: TGA 2950 TA Instruments
Scanning Parameters:
Heating between 25-500 C.°.
Heating rate: 10 C.°/min.
Purging with 60 ml/min N2 flow.
Sample weight: 5-10 mg, open platinum pan

EXAMPLES

Reference Examples

Boc-Saxagliptin used in any of the above described processes may be prepared according to US 2005/0090539, which is incorporated herein by reference.

Saxagliptin hydrochloride dihydrate form H2-1 used in any of the above described processes may be prepared according to US 2009/054303 example 5, which is incorporated herein by reference.

Starting Materials:

Preparation of Starting Material: Boc-Saxagliptin (S)—N-Boc-3-hydroxyadamantylglycine-L-cis-4,5-methanoprolinamide ("AMSG") (23 g, 53.05 mmol) was dissolved in technical distilled dichloromethane (DCM) (115 mL) at 0° C. in three necked round bottom flask. A colorless to light yellow solution was obtained. To this solution, triethylamine (22.1 ml, 159.15 mmol) was added without any visible change, and the resulting reaction mixture was stirred for 30 minutes at 0° C. During a time period of 30 minutes, trichloroacetyl chloride (7.7 ml, 68.9 mmol) in technical distilled DCM (69 ml) was added dropwise at 0° C. During this addition white smoke was observed. The temperature did not rise above 7° C. Five minutes after the addition of trichloroacetyl chloride was complete, the reaction mixture was heated to approximately 10° C., and 230 ml of $H_2O$ was added, and the mixture was well stirred. The layers were separated in a separation funnel. To the upper (water layer) NaCl was added (⅔ saturated solution of NaCl), and this aqueous layer was extracted twice with 50 ml of technical distilled DCM. The multiple DCM layers were combined, washed once with 140 ml of 20% solution of $KHCO_3$, dried over $MgSO_4$, and evaporated to dryness to provide 24 g of a white to off-white foamy product.

Preparation of Starting Material: Crystalline Mono Hydrochloride Salt of Saxagliptin Dihydrate Form H2-1: according to US 2009/054303, example 5 A.

The Part A compound was prepared as described in Publication No. US2005/0090539 A1 published Apr. 28, 2005 as follows: (4.19 g, 10.1 mmol) was dissolved in anhydrous $CH_2Cl_2$ (25 mL) and cooled to 0° C. and treated with trifluoroacetic acid (15 mL) and stirred for 2.5 h at ambient temperature. The solvents were removed by rotary evaporation and the residue was chased with toluene (5 mL) and dried under reduced pressure. Titration with $Et_2O$ afforded the title compound as a white solid (3.92 g, 90%).

B. Preparation of Crystalline MonoHydrochloride Salt of Saxagliptin Dihydrate (Form H2-1)

50 Mg of the trifluoroacetic acid (TFA) salt (potency: 92%) of saxagliptin was dissolved in 0.2 mL water. The pH of the resulting aqueous solution was adjusted to approximately 9.4 with 1N NaOH. Aqueous and organic layers were formed. The aqueous layer was extracted with 2×0.5 mL methylene chloride. The combined rich methylene chloride solution was washed with 1 mL water. 0.116 mL (1 equiv.) of a solution of 1N HCl was added to the rich methylene chloride solution. A clear solution formed which was evaporated to dryness leaving a solid. 0.2 mL of ethanol was mixed with the solid to dissolve the solid. The resulting ethanol solution was heated to 45° C. and 0.3 mL of t-butylmethyl ether was added. The solution turned into a slurry. The slurry was cooled from 45° C. to 20° C. over one hour. The cooled slurry was filtered and the resulting filter cake was dried at room temperature under vacuum to obtain monohydrochloride salt of saxagliptin dihydrate (form H2-1).

Preparation of Starting Material: (1S,3S,5S)-2-[(2S)-2-propan-2-ylideneamino-2-(3-hydroxy-1-adamantyl)acetyl]-2-azabicyclo[3.1.0]hexane-3-carbonitrile ("Compound M")

Amorphous Saxagliptin was placed in a Petri dish in a desiccator in an acetone atmosphere at room temperature. After 24 hours the sample was analyzed by PXRD. Crystalline compound M was obtained.

Preparation of Starting Material: Amorphous Saxagliptin According to IPCOM000195128D Boc-Saxagliptin (5.25 g; 12.63 mmol) was dissolved in 2-PrOH (6.7 mL), and water (6.3 mL) was added. Concentrated HCl (0.21 mL, 2.52 mmol) was added at room temperature with stirring. The reaction mixture was heated to 65° C. and conc. HCl (1.27 mL; 15.14 mmol) was added dropwise to the reaction mixture over 5 minutes while maintaining the temperature at 65° C. The reaction mixture was then stirred at 65° C. for 2 hours. The mixture was then cooled down to room temperature which resulted in the formation of a precipitate. Water (10.5 mL) and dichloro-methane (31.5 mL) were added to the reaction mixture followed by addition of 10M NaOH (1.10 mL; 12.67 mmol) and 1.05 mL of water for washing. Aqueous potassium carbonate (25% wt. solution, 5.6 mL) was added to adjust the pH to 9. This was followed by addition of water (1.05 mL) and NaCl (6.56 g; 0.115 mol). At this point, the pH dropped to 8.48, so an additional amount of the $K_2CO_3$ solution was added (1.0 mL) to adjust the pH back to 9. The resulting mixture was then stirred at room temperature for 30 minutes after which the two-phase mixture was separated. The separated water layer was extracted with dichloromethane (4×50 mL). The organic layers were combined and evaporated to dryness under reduced pressure yielding 4.11 g of crude Saxagliptin.

The crude Saxagliptin residue was purified by flash chromatography using $CH_2Cl_2$/MeOH/$NH_3$ (25% wt. sol.) 5:1:0.1 as an eluent. The fractions containing the pure product were combined and evaporated to dryness under reduced pressure with moderate heating (40-43° C.), yielding 3.43 g (86%) of Saxagliptin as white foam.

Preparation of Starting Material: Saxagliptin form H-1

Crystalline compound M was placed in a Petri dish in a desiccator in a water atmosphere—100% relative humidity at room temperature. After 24 hours the sample was analyzed by PXRD, and the crystalline product was found to be form H-1.

Preparation of Starting Material: Saxagliptin Hydrochloride H 1.25-2

Boc-Saxagliptin (1 g) was dissolved in n-propanol (PrOH) (5 ml), and conc. HCl (0.224 ml) was added. After stirring the mixture at reflux for 1 h, the mixture was cooled to 60° C. and additional conc. HCl (0.224 ml) was added. A thick suspension was obtained and additional PrOH (10 ml) was added. The suspension was cooled and stirred at room temperature (RT) for 30 min and filtered off yielding 234 mg of product.

In all of the examples, unless indicated otherwise the product isolated from the process described in the examples was not subjected to drying step.

Example 1

Preparation of Crystalline Saxagliptin Hydrochloride Form K in a Mixture with Crystalline Saxagliptin Monohydrochloride Dihydrate Form H2-1

Boc-Saxagliptin (1.15 g, 2.76 mmol) was dissolved in acetone (10 ml). Hydrochloric acid (351.5 µl, 4.15 mmol, 36.5%) was added and a suspension was formed. The suspension was heated to reflux temperature and a thick suspension was obtained. Additional acetone (5 ml) was added. The suspension was then refluxed for 1 hour. It was then cooled to room temperature and was filtered. The obtained white crystals were washed with acetone and air dried at room temperature, overnight.

(597 mg).

Example 2

Preparation of Crystalline Saxagliptin Hydrochloride Form K in a Mixture with Crystalline Saxagliptin Monohydrochloride Dihydrate Form H2-1

Boc-Saxagliptin (0.01415 mol, 1 mol eq) was dissolved in acetone (p.a., 90 mL). To this solution was added concentrated HCl solution in water (36.5% equity, 3.60 mL, 0.04245 mol, 1.5 mol eq). The resulting solution was then heated to reflux temperature (70° C.) and was mixed at reflux for 1 hour (about ⅓ of the acetone evaporated from the reaction mixture during the heating). Afterwards, a white precipitate crystallized out. The suspension was cooled to 0-5° C. and then the precipitate was separated by filtration. The precipitate was washed with 10 mL of acetone and dried in vacuum at 40° C. for 2 hours. The powder was characterized by PXRD.

Example 3

Preparation of Crystalline Saxagliptin Hydrochloride Form T in a Mixture with Ammonium Chloride The Schiff base of Saxagliptin (compound M, 1 g) was suspended in 5 ml of saturated $NH_4Cl$ solution (pH=4.53) at room temperature. The suspension was stirred at room temperature overnight. A white crystalline product formed and was filtered off to provide 2.03 g of wet white crystalline product. The product was dried in a vacuum drier under the following conditions: 40° C., 0 bar, 2 hours, to provide 0.97 g of product.

Example 4

Preparation of Crystalline Saxagliptin Hydrochloride Form Z in a Mixture with Form D Saxagliptin hydrochloride, form H2-1 (300 mg) was dissolved in a mixture of 2-butanol (14 ml) and water (0.5 ml) while heating up to 100° C. The resulting solution was then hot filtered and was left to cool down to room temperature while stirring. The stirring was continued for an additional hour at room temperature. The obtained suspension was then filtered under vacuum to yield 179 mg of the product. PXRD is shown in FIG. 5.

Example 5

Preparation of Crystalline Saxagliptin Hydrochloride Form N

Boc-Saxagliptin (1 g, 2.4065 mmol) was dissolved in 2-butanol (10 ml) and HCl (36.5%, 0.448 ml, 2.2 mole equivalent)

was added at about 40° C. and a clear solution was formed. The clear solution was stirred at reflux temperature for 10 minutes. An additional amount of 2-butanol was added (15 ml). The mixture was refluxed for 1.5 hours, and then was left to cool to about 60° C. The crystals that formed were then separated by filtration. The obtained white crystals were washed with 2-butanol and air dried overnight at room temperature to provide 576 mg of Saxagliptin hydrochloride form N (The powder X-ray diffractogram is provided in FIG. 6).

Example 6

Preparation of Crystalline Saxagliptin Hydrochloride Form S

Boc-Saxagliptin (1.0 g) was dissolved in wet ethyl acetate (water saturated, 8.5 ml) and conc. HCl (0.611 ml) was added. The mixture was heated to 70° C. and stirred for 1 h. The resulting suspension was left to cool to about 60° C. and PXRD analysis was carried out on a sample, which was determined to be Form S. The powder X-ray diffractogram is provided in FIG. 7

Example 7

Preparation of Crystalline Saxagliptin Hydrochloride Form O in a Mixture with Crystalline Saxagliptin Hydrochloride Form K Boc-Saxagliptin (1.0 g) was dissolved in 0.837 M HCl/EtOH (2.2 mol eq; 6.32 ml). The mixture was heated to 80° C. and stirred for 1.5 h. The resulting suspension was left to cool to room temperature and a white solid formed and was separated by filtering (0.88 g; 95%). Form O, in a mixture with form K was obtained. The powder X-ray diffractogram is provided in FIG. 8.

Example 8

Preparation of Crystalline Saxagliptin Hydrochloride Form B in a Mixture with Crystalline Saxagliptin Monohydrochloride Dihydrate form H2-1

Saxagliptin monohydrochloride dihydrate form H2-1 (1.0 g; 2.58 mmol) was dissolved in 96% ethanol (10 ml) at 50° C. and then methyl ethyl ketone (30 mL) was added dropwise. The resulting mixture was then left to cool to room temperature and stirred for 1.5 hours. A white precipitate formed and was separated by filtration to provide the product (0.86 g; 86%) which was determined to be a mixture of Form B and H2-1. The powder X-ray diffractogram is provided in FIG. 9

Example 9

Preparation of Crystalline Saxagliptin Hydrochloride Form C

Saxagliptin monohydrochloride dihydrate form H2-1 (1.0 g; 2.58 mmol) was dissolved in PrOH (10 ml) at 100° C. and a clear solution was formed. The solution was left to cool to room temperature and stirred for 1.5 hours. A white precipitate formed and was separated by filtration to provide the product (0.19 g; 19%) which was determined to be Form C. The powder X-ray diffractogram is provided in FIG. 10.

Example 10

Preparation of Crystalline Saxagliptin Hydrochloride Form Z

Saxagliptin monohydrochloride dihydrate Form H2-1 (1.0 g; 2.58 mmol) was dissolved in 96% EtOH (10 ml) at 50° C. and then methyl isopropyl ketone (30 ml) was added dropwise. The resulting mixture was then left to cool to room temperature and stirred for 1.5 hours. A white precipitate formed and was separated by filtration to provide the product (0.85 g; 85%) which was determined by PXRD to be Form Z.

Example 11

Preparation of Crystalline Saxagliptin Hydrochloride Form Z

Saxagliptin monohydrochloride dihydrate Form H2-1 (1.0 g; 2.58 mmol) was dissolved in PrOH (10 mL) at 100° C. and then ethyl acetate (30 ml) was added drop-wise. The resulting mixture was then left to cool to room temperature and stirred for 1.5 hours. A white precipitate formed and was separated by filtration to provide the product (0.60 g; 60%) which was determined by PXRD to be Form Z Example 12

Preparation of Crystalline Saxagliptin Hydrochloride Form Z

Saxagliptin monohydrochloride dihydrate Form H2-1 (1.0 g; 2.58 mmol) was dissolved in PrOH (10 mL) at 100° C. and then 2-methyltetrahydrofuran (30 ml) was added dropwise. The resulting mixture was then left to cool to room temperature and stirred for 1.5 hours. A white precipitate formed and was separated by filtration to provide the product (0.89 g; 89%) which was determined by PXRD to be Form Z.

Example 13

Preparation of Crystalline Saxagliptin Hydrochloride Form Z

Saxagliptin HCl, form H2-1 (300 mg), was dissolved in a mixture of 14 ml of 2-butanol and 0.5 ml of water while heating at reflux (2-butanol has boiling point of 99° C.). The resulting solution was filtered and stirred at room temperature for 1 hour. The obtained suspension was filtered, yielding 179 mg of the product.

Example 14

Preparation of Crystalline Saxagliptin Hydrochloride Form Z in a Mixture with Form D Saxagliptin monohydrate, form H-1 (2 g) was suspended in 15 ml of 1-butanol and a solution of 0.591 ml of conc. HCl in 15 ml of n-butylacetate ("BuOAc") was added dropwise. The obtained suspension was analyzed by PXRD and polymorphically pure form Z was found to have been obtained. The suspension was stirred at room temperature for 30 min and then for additional 30 min in an ice bath. The suspension was then filtered, yielding 1.879 g of Saxagliptin HCl. PXRD is shown in FIG. 12.

Example 15

Preparation of Crystalline Saxagliptin Hydrochloride Form D

Saxagliptin monohydrate, form H-1 (1 g) was suspended in 10 ml of 1-butanol and 0.275 ml of conc. HCl was added. A thick suspension was obtained. An additional 15 ml of 1-butanol were added and the suspension stirred at RT for an additional 30 min. The suspension was then filtered, yielding 640 mg of Saxagliptin HCl, form D.

Example 16

Preparation of Crystalline Saxagliptin Hydrochloride Form Z

Saxagliptin hydrochloride form H1.25-2 (50 mg) was placed in an open Petri-dish and heated in an oven at 100° C. for 2 h. Saxagliptin hydrochloride Form Z was obtained.

Example 17

Preparation of Crystalline Saxagliptin Hydrochloride Form K

Boc-Saxagliptin (1 g) was dissolved in EtOAc (10 ml) and conc. HCl (0.224 ml) was added. The mixture was stirred at reflux for 2.5 hours and additional conc. HCl (0.224 ml) was added. The resulting mixture was stirred at reflux for an additional 30 min and then cooled to 30° C. The mixture was then placed in an ice bath and stirred for 1 h. A suspension formed. The suspension was filtered yielding 633 mg of the product.

Example 18

Preparation of Amorphous Saxagliptin Hydrochloride

Boc-Saxagliptin (1.0 g, 0.0024 mol, and 1 mol eq) was dissolved in dry ethanol (10 ml) and to this solution was added ethanolic HCl (0.84 M HCl, 3.14 ml, 0.0026 mol, 1.1 mol eq). The resulting mixture was heated to reflux temperature (80° C.) and stirred for 2 hours. At this time, additional ethanolic HCl (3.14 ml, 0.0026 mol, 1.1 mol eq) was added, and the reaction mixture was stirred for an additional 30 minutes at reflux, forming a clear solution. To this clear solution was added dropwise methyl isobutyl ketone (54 ml) and the resulting mixture was cooled to 20° C. with stirring. The stirring at 20° C. was maintained for 18 hours, during which time, a gelatinous product precipitated. The product was separated by filtration. The precipitate was dried in vacuum at 40° C. for 2 hours to provide a powder (0.72 g; 77%), which was characterized by PXRD.

Example 19

Preparation of Amorphous Saxagliptin Hydrochloride

Boc-Saxagliptin (1.0 g, 0.0024 mol, and 1 mol eq) was dissolved in dry ethanol (10 ml), and to this solution was added ethanolic HCl (0.84 M HCl in dry ethanol; 3.14 ml; 0.0026 mol; 1.1 mol eq). The resulting mixture was heated to reflux temperature (80° C.) and stirred for 2 hours. At this time, additional ethanolic HCl (3.14 ml, 0.0026 mol, 1.1 mol eq) was added, and reaction mixture was stirred for an additional 30 minutes at reflux, forming a clear solution. To this clear solution was added dropwise isopropyl acetate (54 ml) and the resulting mixture was then cooled to 20° C. with stirring. The stirring at 20° C. was maintained for 18 hours, during which time, a gelatinous product precipitated. The precipitate was separated by filtration. The precipitate was then dried under vacuum at 40° C. for 2 hours to provide a powder (0.70 g; 75%) which was characterized by PXRD.

Example 20

Preparation of Amorphous Saxagliptin Hydrochloride

Boc-Saxagliptin (1.0 g, 0.0024 mol, and 1 mol eq) was dissolved in dry ethanol (10 ml) and to this solution was added ethanolic HCl (0.84 M HCl in dry ethanol; 3.14 ml; 0.0026 mol; 1.1 mol eq). The resulting mixture was heated to reflux temperature (80° C.) and stirred for 2 hours. At this time, additional ethanolic HCl (3.14 ml, 0.0026 mol, 1.1 mol eq) was added, and the reaction mixture was stirred for an additional 30 minutes at reflux forming a clear solution. To this clear solution was added dropwise n-butyl acetate (54 ml) and the resulting mixture was then cooled to 20° C. with stirring. The stirring at 20° C. was maintained for 18 hours, during which time, a gelatinous product precipitated. The precipitate was separated by filtration. The precipitate was then dried under vacuum at 40° C. for 2 hours to provide a powder (0.75 g; 81%) which was characterized by PXRD.

Example 21

Preparation of Crystalline Saxagliptin Hydrochloride Form Z

A solution of Saxagliptin (monohydrate, 4.5 g) in 1-butanol ("1-BuOH", 68 ml) was warmed up to 40° C. and conc. Conc. HCl was added (1.258 ml). The resulting mixture was stirred at the same temperature for 30 min and a suspension was formed. The suspension was cooled to 20° C. and butyl acetate ("BuOAc" 68 ml) was added dropwise. The suspension was cooled to 0° C. and stirred for 2 h. The suspension was filtered, and the collected crystalline solid was washed with cool 1-BuOH/BuOAc (1/1) mixture yielding 3.92 g of the product. PXRD is shown in FIG. 18.

Example 22

Preparation of Crystalline Saxagliptin Hydrochloride Form D

Saxagliptin hydrochloride (0.7 g, a mixture of form Z and form D) was slurried in a mixture of n-butanol (7 ml) and water (0.124 ml) for 36 hours at room temperature. The resulting suspension was filtered, yielding 494 mg of white crystals. The product was analyzed by PXRD, which showed that Form D was obtained.

What is claimed:
1. Crystalline Saxagliptin hydrochloride Form K, characterized by a powder XRD pattern having peaks at 6.4, 11.4, 12.8, 15.7, and 19.4 degrees 2-theta±0.2 degrees 2-theta.
2. The crystalline Saxagliptin hydrochloride Form K of claim 1, further characterized by a powder XRD pattern substantially as depicted in FIG. 16.

3. The crystalline Saxagliptin hydrochloride Form K of claim 1, further characterized by additional powder XRD peaks at 5.4, 14.8, 16.7, and 22.1 degrees 2-theta±0.2 degrees 2-theta.

4. The crystalline Saxagliptin hydrochloride Form K of claim 1, further characterized by one, two, three, or four additional powder XRD peaks selected from 5.4, 14.8, 16.7, and 22.1 degrees two theta±0.2 degrees two theta.

5. Crystalline Saxagliptin hydrochloride Form Z, characterized by an X-ray powder diffraction pattern having peaks at 9.3, 12.0, 14.2 and 19.2 degrees two theta±0.2 degrees two theta.

6. The crystalline Saxagliptin hydrochloride Form Z of claim 5, further characterized by an X-ray powder diffraction pattern substantially as depicted in FIG. 18.

7. The crystalline Saxagliptin hydrochloride Form Z of claim 5, further characterized by additional X-ray powder diffraction peaks at 8.1, 16.6 and 23.2 degrees two theta±0.2 degrees two theta.

8. Crystalline Saxagliptin hydrochloride Form D, characterized by an X-ray powder diffraction pattern having peaks at 10.6, 14.4, 15.4, 17.3, 22.6 and 25.7 degrees two theta±0.2 degrees two theta.

9. The crystalline Saxagliptin hydrochloride Form D of claim 8, further characterized by a powder XRD pattern substantially as depicted in FIG. 11.

10. The crystalline Saxagliptin hydrochloride Form D of claim 8, further characterized by an X-ray powder diffraction pattern having peaks at 8.6 and 19.0 degrees two theta±0.2 degrees two theta.

11. A process of preparing a Saxagliptin hydrochloride solid state form selected from: monohydrate form H-1, hemihydrate form H0.5-2, dihydrate form H2-1, anhydrous form N-3 or any mixture thereof, said process comprising converting the solid state form of Saxagliptin hydrochloride according to any one of claim 1, 5 and 8 to said solid state form selected from: monohydrate form H-1, hemihydrate form H0.5-2, dihydrate form H2-1, anhydrous form N-3 or mixture thereof.

12. A pharmaceutical composition comprising a solid state form of Saxagliptin hydrochloride according to any one of claim 1, 5, and 8; or any combination of said solid state forms, and at least one pharmaceutically acceptable excipient.

13. A method of treating a patient suffering from type 2 diabetes, comprising administering a pharmaceutical composition according to claim 12.

14. The crystalline Saxagliptin hydrochloride Form K of claim 1, further characterized by a solid-state $^{13}$C NMR spectrum having characteristic peaks at 167.0, 120.2, 58.8, 45.3 and 30.5 ppm±0.2 ppm.

15. The crystalline Saxagliptin hydrochloride Form K of claim 1, further characterized by a solid-state $^{13}$C NMR spectrum substantially as depicted in FIG. 19.

16. The crystalline Saxagliptin hydrochloride Form Z of claim 5, further characterized by a solid-state $^{13}$C NMR spectrum having characteristic peaks at 46.5, 44.9, 42.5 and 29.1 ppm,±0.1 ppm.

17. The crystalline Saxagliptin hydrochloride Form Z of claim 5, further characterized by a solid-state $^{13}$C NMR spectrum substantially as depicted in any one of FIGS. 20-21.

18. The crystalline Saxagliptin hydrochloride Form D of claim 8, further characterized by a solid-state $^{13}$C NMR spectrum having characteristic peaks at 46.2, 44.8, 42.3, 32.1 and 14.7 ppm±0.1 ppm.

19. The crystalline Saxagliptin hydrochloride Form D of claim 8, further characterized by a solid-state $^{13}$C NMR spectrum substantially as depicted in any one of FIGS. 22-23.

* * * * *